(12) United States Patent
Lake et al.

(10) Patent No.: US 12,306,175 B2
(45) Date of Patent: May 20, 2025

(54) BIOMARKERS FOR DETECTION AND TREATMENT ASSESSMENT OF INFECTIOUS DISEASES AND DISORDERS

(71) Applicants: Arizona Board of Regents on behalf of Arizona State University, Scottsdale, AZ (US); MAYO FOUNDATION FOR MEDICAL EDUCATION AND RESEARCH, Rochester, MN (US)

(72) Inventors: Douglas Lake, Scottsdale, AZ (US); Haiwei Gu, Scottsdale, AZ (US); Thomas Grys, Scottsdale, AZ (US); Natalie Mitchell, Phoenix, AZ (US); Paniz Jasbi, Mesa, AZ (US)

(73) Assignees: Arizona Board of Regents on behalf of Arizona State University, Scottsdale, AZ (US); MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 994 days.

(21) Appl. No.: 16/992,247

(22) Filed: Aug. 13, 2020

(65) Prior Publication Data
US 2021/0048428 A1 Feb. 18, 2021

Related U.S. Application Data

(60) Provisional application No. 62/887,062, filed on Aug. 15, 2019.

(51) Int. Cl.
*G01N 33/48* (2006.01)
*G01N 33/49* (2006.01)
*G01N 33/493* (2006.01)
*G01N 33/50* (2006.01)
*G01N 33/62* (2006.01)

(52) U.S. Cl.
CPC .......... *G01N 33/50* (2013.01); *G01N 33/492* (2013.01); *G01N 33/493* (2013.01); *G01N 33/62* (2013.01); *G01N 33/48* (2013.01); *G01N 2800/26* (2013.01)

(58) Field of Classification Search
CPC .................................................... G01N 33/48
See application file for complete search history.

(56) References Cited

PUBLICATIONS

Klomp et al. (Am. J. Hum. Genet. Dec. 2000; 67 (6): 1389-99).*
Cokun et al. (Turk. J. Pediatr. Nov.-Dec. 2009; 51 (6): 587-92).*
Jasbi et al. (J. Proteome Res. Jul. 5, 2019; 18 (7): 2791-802).*
Galgiani (Drugs. Oct. 1983; 26 (4): 355-63).*
Li et al. (Cell Death Dis. Apr. 19, 2023; 14 (4): 276; pp. 1-12).*
Ciftci et al. (Acta Trop. Sep. 2021; 221: 105985; pp. 1-8).*
Chen et al. (Biomed. Chromatogr. Apr. 2024; 38 (4): e5817).*
Ahn, J.; Kim, J.; Hwang, J.; Song, J.; Kim, K.; Cha, H.-S. Urinary Metabolomic Profiling to Identify Potential Biomarkers for the Diagnosis of Behcet's Disease by Gas Chromatography/Time-of-Flight-Mass Spectrometry. Int. J. Mol. Sci. 2017, 18 (11), 2309. https://doi.org/10.3390/ijms18112309.
Albuquerque, P.; Paes, H. C.; Tavares, A. H.; Fernandes, L.; Bocca, A. L.; Silva-Pereira, I.; Sueli Soares Felipe, M.; Moraes Nicola, A. Transcriptomics of the Host-Pathogen Interaction in Paracoccidioidomycosis. In Transcriptomics in Health and Disease; Springer International Publishing: Cham, 2014; pp. 265-287. https://doi.org/10.1007/978-3-319-11985-4_14.
Alves de Castro, P.; dos Reis, T. F.; Dolan, S. K.; Oliveira Manfiolli, A.; Brown, N. A.; Jones, G. W.; Doyle, S.; Riaño-Pachón, D. M.; Squina, F. M.; Caldana, C.; et al. The Aspergillus Fumigatus SchA SCH9 Kinase Modulates SakA HOG1 Map Kinase Activity and It Is Essential for Virulence. Mol. Microbiol. 2016, 102 (4), 642-671. https://doi.org/10.1111/mmi. 13484.
Ampel, N. M. The Diagnosis of Coccidioidomycosis. F1000 Med. Rep. 2010, 2. https://doi.org/10.3410/M2-2.
Bartz, F. E.; Glassbrook, N. J.; Danehower, D. A.; Cubeta, M. A. Modulation of the Phenylacetic Acid Metabolic Complex by Quinic Acid Alters the Disease-Causing Activity of Rhizoctonia Solani on Tomato. Phytochemistry 2013, 89, 47-52. https://doi.org/10.1016/j.phytochem.2012.09.018.
Belenky, P.; Bogan, K. L.; Brenner, C. Nad+ Metabolism in Health and Disease. Trends Biochem. Sci. 2007, 32 (1), 12-19. https://doi.org/10.1016/j.tibs.2006.11.006.
Berber, A.; Gómez-Santos, R.; Fanghänel, G.; Sánchez-Reyes, L. Anthropometric Indexes in the Prediction of Type 2 Diabetes Mellitus, Hypertension and Dyslipidemia in a Mexican Population. Int. J. Obes. 2001, 25 (12), 1794-1799. https://doi.org/10.1038/sj.ijo.0801827.
Bills, G. F.; Gloer, J. B. Biologically Active Secondary Metabolites from the Fungi. In The Fungal Kingdom; American Society of Microbiology, 2016; vol. 4, pp. 1087-1119. https://doi.org/10.1128/microbiolspec.FUNK-0009-2016.
Blair, J. E.; Coakley, B.; Santelli, A. C.; Hentz, J. G.; Wengenack, N. L. Serologic Testing for Symptomatic Coccidioidomycosis in Immunocompetent and Immunosuppressed Hosts. Mycopathologia 2006, 162 (5), 317-324. https://doi.org/10.1007/s11046-006-0062-5.
Bowers, J.; Hughes, E.; Skill, N.; Maluccio, M.; Raftery, D. Detection of Hepatocellular Carcinoma in Hepatitis C Patients: Biomarker Discovery by LC-MS. J. Chromatogr. B 2014, 966, 154-162. https://doi.org/10.1016/j.jchromb.2014.02.043.
Brown, A. J. P.; Brown, G. D.; Netea, M. G.; Gow, N. A. R. Metabolism Impacts upon Candida Immunogenicity and Pathogenicity at Multiple Levels. Trends Microbiol. 2014, 22 (11), 614-622. https://doi.org/10.1016/j.tim.2014.07.001.

(Continued)

*Primary Examiner* — Stephen L Rawlings
(74) *Attorney, Agent, or Firm* — Riverside Law LLP

(57) ABSTRACT

The present invention relates to compositions and methods relating to biomarkers that can be used for detection and treatment assessment of infectious diseases or disorders, such as fungal infection, in a subject. The present invention also provides methods of diagnosing infectious diseases or disorders and distinguishing between different types of infectious diseases or disorders (e.g., fungal infection vs bacterial infection). The present invention additionally provides kits that find use in the practice of the methods of the invention.

2 Claims, 20 Drawing Sheets

(56) References Cited

PUBLICATIONS

Buas, M. F.; Gu, H.; Djukovic, D.; Zhu, J.; Onstad, L.; Reid, B. J.; Raftery, D.; Vaughan, T. L. Candidate Serum Metabolite Biomarkers for Differentiating Gastroesophageal Reflux Disease, Barrett's Esophagus, and High-Grade Dysplasia/Esophageal Adenocarcinoma. Metabolomics 2017, 13 (3), 23. https://doi.org/10.1007/s11306-016-1154-y.

Carroll, P. A.; Diolaiti, D.; McFerrin, L.; Gu, H.; Djukovic, D.; Du, J.; Cheng, P. F.; Anderson, S.; Ulrich, M.; Hurley, J. B.; et al. Deregulated Myc Requires MondoA/Mix for Metabolic Reprogramming and Tumorigenesis. Cancer Cell 2015, 27 (2), 271-285. https://doi.org/10.1016/J.CCELL.2014.11.024.

Chang, D. C.; Anderson, S.; Wannemuehler, K.; Engelthaler, D. M.; Erhart, L.; Sunenshine, R. H.; Burwell, L. A.; Park, B. J. Testing for Coccidioidomycosis among Patients with Community-Acquired Pneumonia. Emerg. Infect. Dis. 2008, 14 (7), 1053-1059. https://doi.org/10.3201/eid1407.070832.

Chitty, J. L.; Blake, K. L.; Blundell, R. D.; Koh, Y. Q. A. E.; Thompson, M.; Robertson, A. A. B.; Butler, M. S.; Cooper, M. A.; Kappler, U.; Williams, S. J.; et al. Cryptococcus Neoformans ADS Lyase Is an Enzyme Essential for Virulence Whose Crystal Structure Reveals Features Exploitable in Antifungal Drug Design. J. Biol. Chem. 2017, 292 (28), 11829-11839. https://doi.org/10.1074/jbc.M117.787994.

Chong, J.; Soufan, O.; Li, C.; Caraus, I.; Li, S.; Bourque, G.; Wishart, D. S.; Xia, J. MetaboAnalyst 4.0: Towards More Transparent and Integrative Metabolomics Analysis. Nucleic Acids Res. 2018, 1 (1), 9. https://doi. org/10.1093/nar/gky310.

Ciebiada-Adamiec, A.; Małafiej, E.; Ciebiada, I. Inhibitory Effect of Nicotinamide on Enzymatic Activity of Selected Fungal Strains Causing Skin Infection. Mycoses 2010, 53 (3), 204-207. https://doi.org/10.1111/j. 1439-0507.2009.01696.x.

Crum, N. F.; Lederman, E. R.; Stafford, C. M.; Parrish, J. S.; Wallace, M. R. Coccidioidomycosis: A Descriptive Survey of a Reemerging Disease. Clinical Characteristics and Current Controversies. Medicine (Baltimore). 2004, 83 (3), 149-175. https://doi.org/10.1097/01.md.0000126762.91040.fd.

Culibrk, L.; Croft, C. A.; Tebbutt, S. J. Systems Biology Approaches for Host-Fungal Interactions: An Expanding Multi-Omics Frontier. Omi. A J. Integr. Biol. 2016, 20 (3), 127-138. https://doi.org/10.1089/omi.2015.0185.

Dadwal, S. S.; Kontoyiannis, D. P. Recent Advances in the Molecular Diagnosis of Mucormycosis. Expert Rev. Mol. Diagn. 2018, 18 (10), 845-854. https://doi.org/10.1080/14737159.2018.1522250.

Durkin, M.; Connolly, P.; Kuberski, T.; Myers, R.; Kubak, B. M.; Bruckner, D.; Pegues, D.; Wheat, L. J. Diagnosis of Coccidioidomycosis with Use of the Coccidioides Antigen Enzyme Immunoassay. Clin. Infect. Dis. 2008, 47 (8), e69-e73. https://doi.org/10.1086/592073.

Eisenreich, W.; Heesemann, J.; Rudel, T.; Goebel, W. Metabolic Adaptations of Intracellullar Bacterial Pathogens and Their Mammalian Host Cells during Infection ("Pathometabolism"). Microbiol. Spectr. 2015, 3 (3). https://doi.org/10.1128/microbiolspec.MBP-0002-2014.

Ellis, D. I.; Goodacre, R. Metabolic Fingerprinting in Disease Diagnosis: Biomedical Applications of Infrared and Raman Spectroscopy. Analyst 2006, 131 (8), 875. https://doi.org/10.1039/b602376m.

Emwas, A.-H. M.; Salek, R. M.; Griffin, J. L.; Merzaban, J. NMR-Based Metabolomics in Human Disease Diagnosis: Applications, Limitations, and Recommendations. Metabolomics 2013, 9 (5), 1048-1072. https://doi.org/10.1007/s11306-013-0524-y.

Ene, I. V.; Brunke, S.; Brown, A. J. P.; Hube, B. Metabolism in Fungal Pathogenesis. Cold Spring Harb. Perspect. Med. 2014, 4 (12), a019695-a019695. https://doi.org/10.1101/cshperspect.a019695.

Fisher, F. S.; Bultman, M. W.; Johnson, S. M.; Pappagianis, D.; Zaborsky, E. Coccidioides Niches and Habitat Parameters in the Southwestern United States: A Matter of Scale. Ann. N. Y. Acad. Sci. 2007, 1111 (1), 47-72. https://doi.org/10.1196/annals.1406.031.

Galgiani, J. N.; Ampel, N. M.; Blair, J. E.; Catanzaro, A.; Johnson, R. H.; Stevens, D. A.; Williams, P. L. Coccidioidomycosis. Clin. Infect. Dis. 2005, 41 (9), 1217-1223. https://doi.org/10.1086/496991.

Gowda, G. N.; Metabolomics, D. R. Biomarker Discovery and Translation in Metabolomics. Curr. Metabolomics 2013, 1 (3), 227-240.

Grys, T.; Brighton, A.; Chang, Y.; Liesman, R.; Bolster, L.; Blair, J. Comparison of Two FDA-Cleared EIA Assays for the Detection of Coccidioides Antibodies against a Composite Clinical Standard. Med. Mycol. 2018, 1-6. https://doi.org/10.1093/mmy/myy094.

Gu, H.; Carroll, P. A.; Du, J.; Zhu, J.; Neto, F. C.; Eisenman, R. N.; Raftery, D. Quantitative Method to Investigate the Balance between Metabolism and Proteome Biomass: Starting from Glycine. Angew. Chemie Int. Ed. 2016, 55 (50), 15646-15650. https://doi.org/10.1002/anie.201609236.

Gu, H.; Gowda, G. N.; Raftery, D. Metabolic Profiling: Are We En Route to Better Diagnostic Tests for Cancer? Futur. Oncol. 2012, 8 (10), 1207-1210. https://doi.org/10.2217/fon.12.113.

Gu, H.; Zhang, P.; Zhu, J.; Raftery, D. Globally Optimized Targeted Mass Spectrometry: Reliable Metabolomics Analysis with Broad Coverage. Anal. Chem. 2015, 87 (24), 12355-12362. https://doi.org/10.1021/acs.analchem.5b03812.

Huang, J. Y.; Bristow, B.; Shafir, S.; Sorvillo, F. Coccidioidomycosis-Associated Deaths, United States, 1990-2008. Emerg. Infect. Dis. 2012, 18 (11), 1723-1728. https://doi.org/10.3201/eid1811.120752.

Increase in Reported Coccidioidomycosis—United States, 1998-2011 https://www.cdc.gov/mmwr/preview/mmwrhtml/mm6212a1.htm?s_cid=mm6212a1_e (accessed Aug. 7, 2018).

Jasbi, P.; Wang, D.; Cheng, S. L.; Fei, Q.; Cui, J. Y.; Liu, L.; Wei, Y.; Raftery, D.; Gu, H. Breast Cancer Detection Using Targeted Plasma Metabolomics. J. Chromatogr. B. Analyt. Technol. Biomed. Life Sci. 2019, 1105, 26-37. https://doi.org/10.1016/j.jchromb.2018.11.029.

Johnson, R.; Kernerman, S. M.; Sawtelle, B. G.; Rastogi, S. C.; Nielsen, H. S.; Ampel, N. M. A Reformulated Spherule-Derived Coccidioidin (Spherusol) to Detect Delayed-Type Hypersensitivity in Coccidioidomycosis. Mycopathologia 2012, 174 (5-6), 353-358. https://doi.org/10.1007/s11046-012-9555-6.

Kaysen, G. A.; Johansen, K. L.; Chertow, G. M.; Dalrymple, L. S.; Kornak, J.; Grimes, B.; Dwyer, T.; Chassy, A. W.; Fiehn, O. Associations of Trimethylamine N-Oxide With Nutritional and Inflammatory Biomarkers and Cardiovascular Outcomes in Patients New to Dialysis. J. Ren. Nutr. 2015, 25 (4), 351-356. https://doi.org/10.1053/j.jrn.2015.02.006.

Lewis, E. R. G.; David, V. R.; Doyle, A. L.; Rajabi, K.; Kiefer, J. A.; Pirrotte, P.; Barker, B. M. Differences in Host Innate Responses among Coccidioides Isolates in a Murine Model of Pulmonary Coccidioidomycosis. Eukaryot. Cell 2015, 14 (10), 1043-1053. https://doi.org/10.1128/EC.00122-15.

Li, R.; Grimm, S. A.; Mav, D.; Gu, H.; Djukovic, D.; Shah, R.; Merrick, B. A.; Raftery, D.; Wade, P. A. Transcriptome and DNA Methylome Analysis in a Mouse Model of Diet-Induced Obesity Predicts Increased Risk of Colorectal Cancer. Cell Rep. 2018, 22 (3), 624-637. https://doi.org/10.1016/j.celrep.2017.12.071.

Madsen, R.; Lundstedt, T.; Trygg, J. Chemometrics in Metabolomics-A Review in Human Disease Diagnosis. Anal. Chim. Acta 2010, 659 (1-2), 23-33. https://doi.org/10.1016/J.ACA.2009.11.042.

Mirbod-Donovan, F.; Schaller, R.; Hung, C.-Y.; Xue, J.; Reichard, U.; Cole, G. T. Urease Produced by Coccidioides Posadasii Contributes to the Virulence of This Respiratory Pathogen. Infect. Immun. 2006, 74 (1), 504-515. https://doi.org/10.1128/IAI.74.1.504-515.2006.

Mitchell, N. M.; Sherrard, A. L.; Dasari, S.; Magee, D. M.; Grys, T. E.; Lake, D. F. Proteogenomic Re-Annotation of Coccidioides Posadasii Strain Silveira. Proteomics 2018, 18 (1), 1700173. https://doi.org/10.1002/pmic.201700173.

Monnerat, G.; Seara, F. A. C.; Evaristo, J. A. M.; Carneiro, G.; Evaristo, G. P. C.; Domont, G.; Nascimento, J. H. M.; Mill, J. G.; Nogueira, F. C. S.; Campos de Carvalho, A. C. Aging-Related Compensated Hypogonadism: Role of Metabolomic Analysis in

(56) References Cited

PUBLICATIONS

Physiopathological and Therapeutic Evaluation. J. Steroid Biochem. Mol. Biol. 2018, 183, 39-50. https://doi.org/10.1016/j.jsbmb.2018.05.005.

Monod, M.; Capoccia, S.; Léchenne, B.; Zaugg, C.; Holdom, M.; Jousson, O. Secreted Proteases from Pathogenic Fungi. Int. J. Med. Microbiol. 2002, 292 (5-6), 405-419. https://doi.org/10.1078/1438-4221-00223.

Narra, H. P.; Shubitz, L. F.; Mandel, M. A.; Trinh, H. T.; Griffin, K.; Buntzman, A. S.; Frelinger, J. A.; Galgiani, J. N.; Orbach, M. J. A Coccidioides Posadasii CPS1 Deletion Mutant Is Avirulent and Protects Mice from Lethal Infection. Infect. Immun. 2016, 84 (10), 3007-3016. https://doi.org/10.1128/IAI.00633-16.

Paniz Jasi et al., Accurate Coccidioidomycosis Detection Using Targeted Plasma and Urine Metabolic Profiling, Proceedings of the 63rd Coccidioidomycosis Study Group Annual Meeting, Apr. 5, 2019.

Patti, G. J.; Yanes, O.; Siuzdak, G. Metabolomics: The Apogee of the Omics Trilogy. Nat. Rev. Mol. Cell Biol. 2012, 13 (4), 263-269. https://doi.org/10.1038/nrm3314.

Petrini, B.; Sköld, C. M.; Bronner, U.; Elmberger, G. Coccidioidomycosis Mimicking Lung Cancer. Respiration. 2003, 70 (6), 651-654. https://doi.org/10.1159/000075215.

Poddighe, S.; Murgia, F.; Lorefice, L.; Liggi, S.; Cocco, E.; Marrosu, M. G.; Atzori, L. Metabolomic Analysis Identifies Altered Metabolic Pathways in Multiple Sclerosis. Int. J. Biochem. Cell Biol. 2017, 93, 148-155. https://doi.org/10.1016/j.biocel.2017.07.004.

Roy, S.; Nuckles, E.; Archbold, D. D. Effects of Phenolic Compounds on Growth of *Colletotrichum* Spp. In Vitro. Curr. Microbiol. 2018, 75 (5), 550-556. https://doi.org/10.1007/s00284-017-1415-7.

Rubert, J.; Righetti, L.; Stranska-Zachariasova, M.; Dzuman, Z.; Chrpova, J.; Dall'Asta, C.; Hajslova, J. Untargeted Metabolomics Based on Ultra-High-Performance Liquid Chromatography-High-Resolution Mass Spectrometry Merged with Chemometrics: A New Predictable Tool for an Early Detection of Mycotoxins. Food Chem. 2017, 224, 423-431. https://doi.org/10.1016/j.foodchem.2016.11.132.

Santos, R. C. V.; Moresco, R. N.; Peña Rico, M. A.; Susperregui, A. R. G.; Rosa, J. L.; Bartrons, R.; Ventura, F.; Mário, D. N.; Alves, S. H.; Tatsch, E.; et al. Fructose-1,6-Bisphosphate Reduces the Mortality in Candida Albicans Bloodstream Infection and Prevents the Septic-Induced Platelet Decrease. Inflammation 2012, 35 (4), 1256-1261. https://doi.org/10.1007/s10753-012-9436-7.

Savelieff, M. G.; Pappalardo, L. Novel Cutting-Edge Metabolite-Based Diagnostic Tools for Aspergillosis. PLOS Pathog. 2017, 13 (9), e1006486. https://doi.org/10.1371/journal.ppat.1006486.

Sharpton, T. J.; Stajich, J. E.; Rounsley, S. D.; Gardner, M. J.; Wortman, J. R.; Jordar, V. S.; Maiti, R.; Kodira, C. D.; Neafsey, D. E.; Zeng, Q.; et al. Comparative Genomic Analyses of the Human Fungal Pathogens Coccidioides and Their Relatives. Genome Res. 2009, 19 (10), 1722-1731. https://doi.org/10.1101/gr.087551.108.

Smith, C.; Whiting, E.; EE Baker. The Use of Coccidioidin. Am. Rev. Tuberc. 1948, 57, 330-360.

Spinelli, J. B.; Yoon, H.; Ringel, A. E.; Jeanfavre, S.; Clish, C. B.; Haigis, M. C. Metabolic Recycling of Ammonia via Glutamate Dehydrogenase Supports Breast Cancer Biomass. Science (80-. ). 2017, 358 (6365), 941-946. https://doi.org/10.1126/science.aam9305.

Summary of Notifiable Infectious Diseases https://www.cdc.gov/mmwr/mmwr_nd/index.html (accessed Aug. 7, 2018).

Thompson, G. Pulmonary Coccidioidomycosis. Semin. Respir. Crit. Care Med. 2011, 32 (06), 754-763. https://doi.org/10.1055/s-0031-1295723.

Tsang, C. A.; Anderson, S. M.; Imholte, S. B.; Erhart, L. M.; Chen, S.; Park, B. J.; Christ, C.; Komatsu, K. K.; Chiller, T.; Sunenshine, R. H. Enhanced Surveillance of Coccidioidomycosis, Arizona, USA, 2007-2008. Emerg. Infect. Dis. 2010, 16 (11), 1738-1744. https://doi.org/10.3201/eid1611.100475.

Valdivia, L.; Nix, D.; Wright, M.; Lindberg, E.; Fagan, T.; Lieberman, D.; Stoffer, T.; Ampel, N. M.; Galgiani, J. N. Coccidioidomycosis as a Common Cause of Community-Acquired Pneumonia. Emerg. Infect. Dis. 2006, 12 (6), 958-962. https://doi.org/10.3201/eid1206.060028.

Wack, E. E.; Ampel, N. M.; Sunenshine, R. H.; Galgiani, J. N. The Return of Delayed-Type Hypersensitivity Skin Testing for Coccidioidomycosis. Clin. Infect. Dis. 2015, 61 (5), 787-791. https://doi.org/10.1093/cid/civ388.

Wang, D.; Cheng, S. L.; Fei, Q.; Gu, H.; Raftery, D.; Cao, B.; Sun, X.; Yan, J.; Zhang, C.; Wang, J. Metabolic Profiling Identifies Phospholipids as Potential Serum Biomarkers for Schizophrenia. Psychiatry Res. 2019, 272, 18-29. https://doi.org/10.1016/j.psychres.2018.12.008.

Whiston, E.; Zhang Wise, H.; Sharpton, T. J.; Jui, G.; Cole, G. T.; Taylor, J. W. Comparative Transcriptomics of the Saprobic and Parasitic Growth Phases in *Coccidioides* Spp. PLoS One 2012, 7 (7), e41034. https://doi.org/10.1371/journal.pone.0041034.

Wise, H. Z.; Hung, C.-Y.; Whiston, E.; Taylor, J. W.; Cole, G. T. Extracellular Ammonia at Sites of Pulmonary Infection with Coccidioides Posadasii Contributes to Severity of the Respiratory Disease. Microb. Pathog. 2013, 59-60, 19-28. https://doi.org/10.1016/j.micpath.2013.04.003.

Wurtele, H.; Tsao, S.; Lépine, G.; Mullick, A.; Tremblay, J.; Drogaris, P.; Lee, E.-H.; Thibault, P.; Verreault, A.; Raymond, M. Modulation of Histone H3 Lysine 56 Acetylation as an Antifungal Therapeutic Strategy. Nat. Med. 2010, 16 (7), 774-780. https://doi.org/10.1038/nm.2175.

Yin, P.; Xu, G. Metabolomics Toward Biomarker Discovery. In Methods in molecular biology (Clifton, N.J.); 2017; vol. 1619, pp. 467-475. https://doi.org/10.1007/978-1-4939-7057-5_32.

Zhang, A.; Sun, H.; Wang, X. Saliva Metabolomics Opens Door to Biomarker Discovery, Disease Diagnosis, and Treatment. Appl. Biochem. Biotechnol. 2012, 168 (6), 1718-1727. https://doi.org/10.1007/s12010-012-9891-5.

Zhu, J.; Djukovic, D.; Deng, L.; Gu, H.; Himmati, F.; Abu Zaid, M.; Chiorean, E. G.; Raftery, D. Targeted Serum Metabolite Profiling and Sequential Metabolite Ratio Analysis for Colorectal Cancer Progression Monitoring. Anal. Bioanal. Chem. 2015, 407 (26), 7857-7863. https://doi.org/10.1007/s00216-015-8984-8.

Zhu, J.; Djukovic, D.; Deng, L.; Gu, H.; Himmati, F.; Chiorean, E. G.; Raftery, D. Colorectal Cancer Detection Using Targeted Serum Metabolic Profiling. J. Proteome Res. 2014, 13 (9), 4120-4130. https://doi.org/10.1021/pr500494u.

\* cited by examiner

| | | Valley Fever N=48 (%) | Non-VF controls N=99 (%) |
|---|---|---|---|
| Sample type, n (%) | Plasma | 18 (37.5) | 41 (41) |
| | Urine | 30 (62.5) | 58 (59) |
| Antifungal meds, n (%) | Yes | 25 (52) | |
| | No/Unknown | 23 (48) | |
| Clinical Course[a] | | | |
| Plasma | Acute | 10 (56) | |
| | Chronic | 4 (22) | |
| | Disseminated | 4 (22) | |
| Urine | Acute | 23 (77) | |
| | Chronic | 4 (13) | |
| | Disseminated | 3 (10) | |
| Serology (EIA, CF or ID)[a] | | | |
| Plasma | Positive | 10 (55) | |
| | Negative | 3 (17) | |
| | Unknown/Indeterminant | 5 (28) | |
| Urine | Positive | 11 (37) | |
| | Negative | 9 (30) | |
| | Unknown/Indeterminant | 10 (33) | |

[a]EIA: Enzyme immunoassay, CF: Complement fixation assay, ID: Immunodiffusion assay
[b]Chronic disease defined as symptomatic >1yr. Disseminated disease defined as confirmed extrapulmonary disease.

Figure 2

| Metabolic Pathways | Number of Metabolites |
|---|---|
| Alanine, aspartate and glutamate metabolism | 10 |
| Arginine and proline metabolism | 13 |
| Butanoate metabolism | 6 |
| Citrate cycle (TCA cycle) | 11 |
| Cysteine and methionine metabolism | 14 |
| Fatty acid metabolism | 3 |
| Glutathione metabolism | 12 |
| Glycine, serine and threonine metabolism | 6 |
| Glycolysis / Gluconeogenesis | 12 |
| Histidine metabolism | 6 |
| Lysine biosynthesis | 7 |
| Lysine degradation | 6 |
| Nitrogen metabolism | 9 |
| Oxidative phosphorylation | 6 |
| Pentose phosphate pathway | 5 |
| Phenylalanine metabolism | 6 |
| Phenylalanine, tyrosine and tryptophan biosynthesis | 8 |
| Purine metabolism | 10 |
| Pyrimidine metabolism | 6 |
| Pyruvate metabolism | 5 |
| Synthesis and degradation of ketone bodies | 4 |
| Tryptophan metabolism | 10 |
| Tyrosine metabolism | 9 |
| Valine, leucine and isoleucine biosynthesis | 7 |
| Valine, leucine and isoleucine degradation | 5 |

Figure 5

| Assay | Metabolites |
|---|---|
| Globally Optimized Targeted Mass Spectrometry | ~450 identified and ~500 unknowns |
| Targeted Assay of ~200 Metabolites | ~200 metabolites in ~25 metabolic pathways |
| Aqueous Global Profiling | ~1000 MS features, ~300 metabolites |
| Lipid Global Profiling | ~1000 MS features, ~400 lipids |
| GC-MS Profiling | >600 MS features, ~100-200 metabolites |
| GC-MS Flux Analysis | TCA, Glycolysis, Amino Acids, Fatty Acids, etc. |
| Carnitine Analysis | ~40 carnitines |
| Bile Acid Analysis | ~60 bile acids |
| Cardiolipin Analysis | ~50 CPs |
| Quantitative Lipid Targeted Analysis | ~100 Lipids |
| Tryptophan Analysis | ~25 tryptophan metabolites |
| Absolute Quantification | ~30 metabolites |
| Multivariate Statistical Analysis | |

Figure 15

BIOMARKERS FOR DETECTION AND TREATMENT ASSESSMENT OF INFECTIOUS DISEASES AND DISORDERS

CROSS-REFERENCE TO RELATED APPLICATIONS

This application claims the benefit of U.S. Provisional Application No. 62/887,062, filed Aug. 15, 2019, the disclosure of which is hereby incorporated by reference in its entirety.

BACKGROUND OF THE INVENTION

Coccidioidomycosis, also known as Valley fever (VF), is a respiratory infection caused by inhalation of airborne fungal spores of *Coccidioides immitis* or *Coccidioides posadasii*. These category C fungal pathogens are endemic to desert climates with mild winters and arid summers such as those in the southwestern United States, including California, Arizona, New Mexico, and Texas, and parts of northern Mexico and South America. From 1990-2008, 3089 deaths in the United States were attributed to coccidioidomycosis, or roughly 200 per year. In states where VF is endemic, overall incidence is estimated to be 42.6 cases per every 100,000 persons per year. Between 1998 and 2016, Arizona accounted for 51-79% of all reported cases of VF in the United States. In highly-endemic areas such as the Phoenix and Tucson metropolitan areas of Arizona, VF is estimated to account for 15-30% of all community-acquired pneumonias (CAP), and evidence seems to suggest that diagnoses are under-reported due to low testing rates. Therefore, VF is a common threat to human health especially in endemic areas.

Currently, VF is difficult to diagnose due to presentation of vague symptoms that often mimic viral or bacterial pneumonias or even lung cancer. In fact, the majority of people who are exposed to this virulent, dimorphic fungus never seek medical care, and approximately 40% of people who contract the fungal infection present with flu-like symptoms such as fatigue, cough, fever, shortness of breath, headaches, night sweats, muscle or joint pain, and rash, which can persist for weeks to months. Approximately 5-10% of infected people will develop serious, often chronic, lung diseases, while roughly 1% of the patients develop disseminated coccidioidomycosis as the infection spreads from the lungs to other parts of the body resulting in nodules, ulcers, skin lesions, and possible meningitis.

The current mainstay diagnostics for VF are serologic testing methods, which mainly include enzyme immunoassay (EIA), complement fixation (CF), and immunodiffusion (ID). However, no single serological test offers both excellent sensitivity and specificity. Additionally, approximately 10% of immunocompetent patients and 30% of immunosuppressed patients fail to produce an adequate immunological response to the VF infection, especially in the acute phase of disease. Accurate diagnosis therefore relies on a combination of clinical presentation, serology, radiography, histology, and culture. These diagnostic methods are either costly, time-consuming (often greater than 2 weeks in the case of fungal culture), invasive, or indeterminable. Therefore, a fast, cost-effective, highly sensitive and specific method for the detection of VF is critically needed.

There is a need in the art for improved methods of diagnosis and prognosis of infectious diseases and disorders in a subject that monitors levels of biomarkers associated with the infectious diseases and disorders and the treatment of said diseases. The present invention satisfies this unmet need.

SUMMARY OF THE INVENTION

In one aspect, the present inventions provides a method of distinguishing subjects with an infectious disease or disorder from subjects without infectious disease or disorder, the method comprising the steps of obtaining a biological sample from a test subject; analyzing the biological sample with an assay that specifically detects at least one biomarker; detecting the level of the at least one biomarker in the biological sample of the subject; comparing the level of the at least one biomarker in the biological sample to a comparator; determining that the subject has infectious disease or disorder when the at least one biomarker is differentially expressed in the biological sample as compared to the comparator; and administering a treatment of the infectious disease or disorder to the subject.

In various embodiments, the at least one biomarker is inosine, 3-phosphoglyceric acid, cyclic guanosine monophosphate (cGMP), phenylacetic acid, amino valerate, glycocyamine, tryptamine, gentisic acid, p-coumaric acid, N,N'-dicyclohexylurea, fructose-1,6-bisphosphate (F16BP), tetracaine, or any combination thereof. In various embodiments, the at least one biomarker comprises two or more selected from the group consisting of: inosine, 3-phosphoglyceric acid, cGMP, phenylacetic acid, amino valerate, glycocyamine, tryptamine, gentisic acid, p-coumaric acid, N,N'-dicyclohexylurea, F16BP, and tetracaine.

In some embodiments, the infectious disease or disorder is a bacterial infection, a fungal infection, a parasitic infection, a viral infection, or any combination thereof. In one embodiment, the fungal infection is Coccidioidomycosis.

In various embodiments, the biological sample comprises a biological tissue of the subject, a blood sample of the subject, a bodily fluid sample of the subject, a fecal sample of the subject, a plasma sample of the subject, a saliva sample of the subject, a urine sample of the subject, or any combination thereof.

In some embodiments, the assay is mass spectrometry (MS), liquid chromatography (LC), liquid chromatography-mass spectrometry (LC-MS), targeted liquid chromatography-tandem mass spectrometry (LC-MS/MS), high-performance liquid chromatography (HPLC), ultra-performance liquid chromatography (UPLC), ultra-high-performance liquid chromatography (UHPLC), gas chromatography (GC), gas chromatography-mass spectrometry (GC-MS), globally optimized targeted mass spectrometry, targeted assay of about 200 metabolites, aqueous global profiling, liquid global profiling, GC-MS profiling, GC-MS flux analysis, carnitine analysis, lipid targeted analysis, quantitative lipid targeted analysis, tryptophan analysis, absolute quantification, multivariate statistical analysis, dynamic light scattering (DLS), nuclear magnetic resonance (NMR) spectroscopy, ultraviolet-visible (UV/Vis) spectroscopy, infrared (IR) spectroscopy, Raman spectroscopy, or any combination thereof.

In one embodiment, the method comprises using a multidimensional non-linear algorithm to determine if the level of a set of biomarkers in the biological sample is statistically different as compared to the comparator.

In various embodiments, the at least one biomarker is inosine, 3-phosphoglyceric acid, cGMP, or any combination thereof. In one embodiment, the subject is determined to have infectious disease or disorder when the level of the at least one biomarker in the biological sample is increased as compared to the comparator.

In various embodiments, the at least one biomarker that is phenylacetic acid, amino valerate, glycocyamine, tryptamine, gentisic acid, p-coumaric acid, N,N'-dicyclohexylurea, F16BP, tetracaine, or any combination thereof. In one embodiment, the subject is determined to have infectious disease or disorder when the level of the at least one biomarker in the biological sample is decreased as compared to the comparator.

In one embodiment, the treatment is determined based on the level of the at least one biomarker in a subject. In various embodiments, the treatment comprises administering a therapeutically effective amount of a drug. In some embodiments, the drug is an antibiotic, antifungal medication, or any combination thereof.

In one aspect, the present invention also provides a method of assessing an effectiveness of treating an infectious disease or disorder in a subject. In various embodiments, the method comprises a step of obtaining a biological sample from a test subject; a step of analyzing the biological sample with an assay that specifically detects at least one biomarker; a step of detecting the level of the at least one biomarker in the biological sample of the subject; a step of comparing the level of the at least one biomarker in the biological sample to a comparator; a step of determining that the subject has infectious disease or disorder when the at least one biomarker is differentially expressed in the biological sample as compared to the comparator; and a step of administering a treatment of the infectious disease or disorder to the subject.

In one embodiment, the treatment is determined based on the level of the at least one biomarker in a subject; and/or wherein the treatment is adjusted based on the level of the at least one biomarker in a subject.

BRIEF DESCRIPTION OF THE DRAWINGS

The following detailed description of various embodiments of the invention will be better understood when read in conjunction with the appended drawings. For the purpose of illustrating the invention, there are shown in the drawings illustrative embodiments. It should be understood, however, that the invention is not limited to the precise arrangements and instrumentalities of the embodiments shown in the drawings.

FIG. 2 depicts clinical and demographic characteristics of exemplary samples.

FIG. 4, comprising FIG. 4A depicts results that demonstrate CV distribution of plasma metabolites in positive mode detection. FIG. 4B depicts results that demonstrate CV distribution of plasma metabolites in negative mode detection. FIG. 4C depicts results that demonstrate CV distribution of urine metabolites in positive mode detection. FIG. 4D depicts results that demonstrate CV distribution of urine metabolites in negative mode detection.

FIG. 5 depicts examples of metabolic pathways and the corresponding number of metabolites.

FIG. 6, comprising

FIG. 6A depicts volcano plot of 207 plasma metabolites comparing Valley fever/non-Valley fever controls. FIG. 6B depicts volcano plot of 231 urine metabolites comparing Valley fever/non-Valley fever controls.

FIG. 7, comprising FIG. 7A depicts the score plot of 106 significant plasma metabolites accounting for 54.5% of variance. FIG. 7B depicts results of statistical validation of plasma PLS-DA model ($R^2X$ (cum)=0.973, $R^2Y$ (cum)=0.862, $Q^2$ (cum)=0.789) by permutation testing (n=200). FIG. 7C depicts the score plot of 20 significant urinary metabolites accounting for 39.8% of variance. FIG. 7D depicts results of statistical validation of urinary PLS-DA model ($R^2X$ (cum)=0.847, $R^2Y$ (cum)=0.627, $Q^2$ (cum)=0.501) by permutation testing (n=200).

FIG. 8, comprising FIG. 8A depicts results demonstrating that three plasma metabolites were observed to have VIPs>2. FIG. 8B depicts results demonstrating that nine urine metabolites were observed to have VIPs>1.

FIG. 9, comprising FIG. 9A depicts score plot of 3 significant and important plasma metabolites accounting for 66.8% of variance. FIG. 9B depicts results of statistical validation of plasma OPLS-DA model ($R^2X$ (cum)=0.668, $R^2Y$ (cum)=0.739, $Q^2$ (cum)=0.723) by permutation testing (n=200). FIG. 9C depicts score plot of 9 significant and important urinary metabolites accounting for 51.1% of variance. FIG. 9D depicts results of statistical validation of urinary OPLS-DA model ($R^2X$ (cum)=0.302, $R^2Y$ (cum)=0.416, $Q^2$ (cum)=0.389) by permutation testing (n=200).

FIG. 12, comprising FIG. 12A depicts results of ROC analysis of 3-metabolite plasma OPLS-DA model (AUC=0.995 (95% CI: 0.983-1.00), sensitivity=0.944 when specificity=0.976). FIG. 12B depicts results of ROC analysis of 9-metabolite urine OPLS-DA model (AUC=0.929 (95% CI: 0.873-0.985), sensitivity=0.897 when specificity=0.881).

FIG. 13, comprising FIG. 13A depicts results of enrichment analysis using 207 reliably detected plasma metabolites. FIG. 13B depicts results of enrichment analysis using 231 reliably detected urinary metabolites.

FIG. 14, comprising FIG. 14A depicts the metabolome view of pathway analysis comparing VF patients and controls using plasma samples ((1) glycine and serine metabolism, (2) purine metabolism, (3) nicotinate and nicotinamide metabolism, (4) ammonia recycling). FIG. 14B depicts the metabolome view of pathway analysis comparing VF patients and controls using urine samples ((5) nicotinate and nicotinamide metabolism, (6) ammonia recycling, (7) phenylalanine metabolism, and (8) arginine and proline metabolism).

FIG. 15 depicts examples of assays used to analyze at least one biomarker of the present invention.

DETAILED DESCRIPTION

Figure 1:
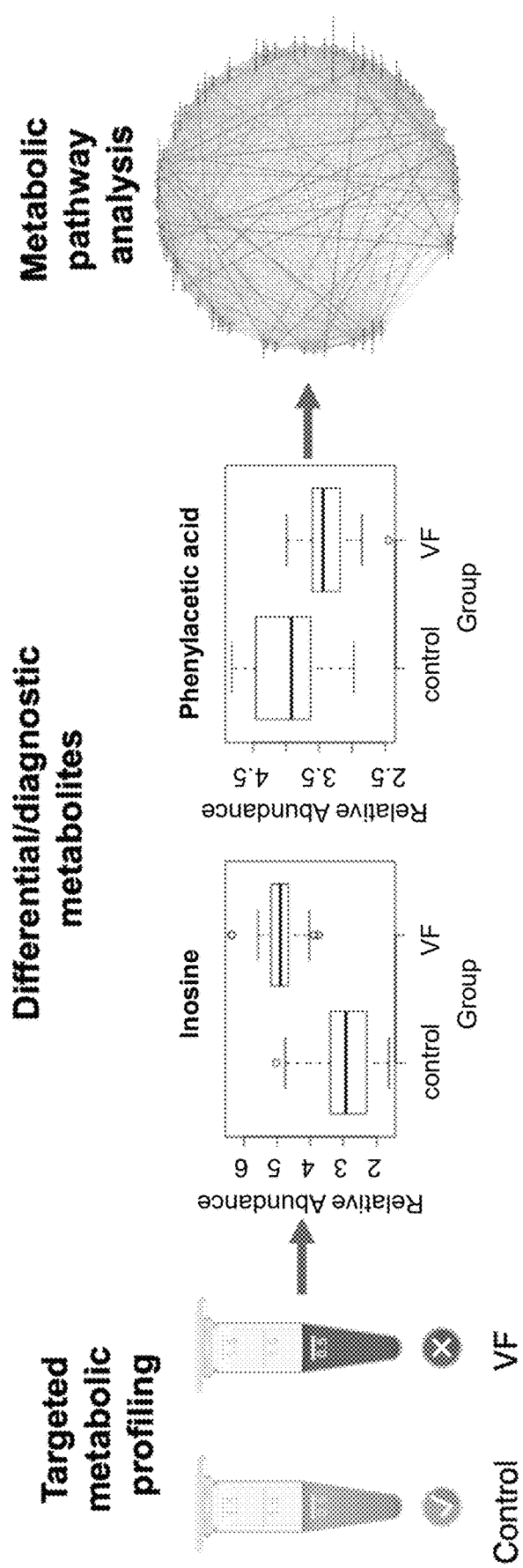
FIG. 1 depicts a schematic representation of the targeted metabolic profiling approach for the rapid and accurate detection of VF.

The present invention is based in part on the discovery that the development and progression of infectious diseases or disorders are associated with an increased inosine level or activity, an increased 3-phosphoglyceric acid level or activity, an increased cyclic guanosine monophosphate (cGMP) level or activity, a decreased phenylacetic acid level or activity, a decreased amino valerate level or activity, a decreased glycocyamine level or activity, a decreased tryptamine level or activity, a decreased gentisic acid level or activity, a decreased p-coumaric acid level or activity, a decreased N,N'-dicyclohexylurea level or activity, a decreased fructose-1,6-bisphosphate (F16BP) level or activity, a decreased tetracaine level or activity, and any combination thereof in a subject. Thus, the invention relates to compositions and methods relating to biomarkers that can be used for identifying, diagnosing, assessing the prognosis of infectious diseases or disorders in a subject. As described herein, an increased inosine level, an increased 3-phosphoglyceric acid level, an increased cGMP level, a decreased phenylacetic acid level, a decreased amino valerate level, a decreased glycocyamine level, a decreased tryptamine level, a decreased gentisic acid level, a decreased p-coumaric acid level, a decreased N,N'-dicyclohexylurea level, a decreased F16BP level, a decreased tetracaine level, and any combinations thereof, is demonstrated to be a useful diagnostic and prognostic biomarker for infectious diseases or disorders. The present invention further provides methods relating to the biomarkers of the invention that can be used to establish and evaluate treatment plans for a subject with an infectious disease or disorder.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

The term "about" will be understood by persons of ordinary skill in the art and will vary to some extent depending on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

The term "abnormal" when used in the context of organisms, tissues, cells or components thereof, refers to those organisms, tissues, cells or components thereof that differ in at least one observable or detectable characteristic (e.g., age, treatment, time of day, etc.) from those organisms, tissues, cells or components thereof that display the "normal" (expected) respective characteristic. Characteristics which are normal or expected for one cell or tissue type, might be abnormal for a different cell or tissue type.

A disease or disorder is "alleviated" if the severity of a sign or symptom of the disease or disorder, the frequency with which such a sign or symptom is experienced by a patient, or both, is reduced.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "diagnosis" refers to the determination of the presence of a disease or disorder. In some embodiments of the present invention, methods for making a diagnosis are provided which permit determination of the presence of a particular disease or disorder.

A "therapeutic" treatment is a treatment administered to a subject who exhibits signs or symptoms of a disease or disorder, for the purpose of diminishing or eliminating those signs or symptoms.

As used herein, "treating a disease or disorder" means reducing the severity and/or frequency with which a sign or symptom of the disease or disorder is experienced by a patient.

The term "derivative" refers to a small molecule that differs in structure from the reference molecule, but retains the essential properties of the reference molecule. A derivative may change its interaction with certain other molecules relative to the reference molecule. A derivative molecule may also include a salt, an adduct, tautomer, isomer, or other variant of the reference molecule.

The term "tautomers" are constitutional isomers of organic compounds that readily interconvert by a chemical process (tautomerization).

The term "isomers" or "stereoisomers" refer to compounds, which have identical chemical constitution, but differ with regard to the arrangement of the atoms or groups in space.

As used herein, "polymorph" refers to crystalline forms having the same chemical composition but different spatial arrangements of the molecules, atoms, and/or ions forming the crystal.

"Pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability. "Pharmaceutically acceptable carrier" refers to a medium that does not interfere with the effectiveness of the biological activity of the active ingredient(s) and is not toxic to the host to which it is administered.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose, and sucrose; starches, such as corn starch and potato starch; cellulose, and its derivatives, such as sodium carboxymethyl cellulose, ethyl cellulose, and cellulose acetate; powdered tragacanth; malt; gelatin; talc; excipients, such as cocoa butter and suppository waxes; oils, such as peanut oil, cottonseed oil, safflower oil, sesame oil, olive oil, corn oil, and soybean oil; glycols, such as propylene glycol; polyols, such as glycerin, sorbitol, mannitol, and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art.

The term "pharmaceutically acceptable salt" refers to any pharmaceutically acceptable salt, which upon administration to the patient is capable of providing (directly or indirectly) a compound as described herein. Such salts preferably are acid addition salts with physiologically acceptable organic or inorganic acids. Examples of the acid addition salts include mineral acid addition salts such as, for example, hydrochloride, hydrobromide, hydroiodide, sulphate, nitrate, phosphate, and organic acid addition salts such as, for example, acetate, trifluoroacetate, maleate, fumarate, citrate, oxalate, succinate, tartrate, malate, mandelate, methane sulphonate, and p-toluenesulphonate. Examples of the alkali addition salts include inorganic salts such as, for example, sodium, potassium, calcium and ammonium salts, and organic alkali salts such as, for example, ethylenediamine, ethanolamine, N,N-dialkylenethanolamine, triethanolamine, and basic amino acids salts. However, it will be appreciated that non-pharmaceutically acceptable salts also fall within the scope of the invention since those may be useful in the preparation of pharmaceutically acceptable salts. Procedures for salt formation are conventional in the art.

The term "solvate" in accordance with this invention should be understood as meaning any form of the active compound in accordance with the invention in which the said compound is bonded by a non-covalent bond to another molecule (normally a polar solvent), including especially hydrates and alcoholates.

The terms "effective amount" and "pharmaceutically effective amount" refer to a sufficient amount of an agent to provide the desired biological result. That result can be reduction and/or alleviation of a sign, symptom, or cause of a disease or disorder, or any other desired alteration of a biological system. An appropriate effective amount in any individual case may be determined by one of ordinary skill in the art using routine experimentation.

A "therapeutically effective amount" refers to that amount which provides a therapeutic effect for a given condition and administration regimen. In particular, "therapeutically effective amount" means an amount that is effective to prevent, alleviate or ameliorate symptoms of the disease or prolong the survival of the subject being treated, which may be a human or non-human animal. Determination of a therapeutically effective amount is within the skill of the person skilled in the art.

As used herein, the term "pharmaceutical composition" refers to a mixture of at least one compound of the invention with other chemical components and entities, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to, intravenous, oral, aerosol, parenteral, ophthalmic, pulmonary and topical administration.

The term "nutritional composition" may be a food product intended for human consumption, for example, a beverage, a drink, a bar, a snack, an ice cream, a dairy product, for example a chilled or a shelf-stable dairy product, a fermented dairy product, a drink, for example a milk-based drink, an infant formula, a growing-up milk, a confectionery product, a chocolate, a cereal product such as a breakfast cereal, a sauce, a soup, an instant drink, a frozen product intended for consumption after heating in a microwave or an oven, a ready-to-eat product, a fast food or a nutritional formula.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

"Instructional material", as that term is used herein, includes a publication, a recording, a diagram, or any other medium of expression which can be used to communicate the usefulness of the nucleic acid, peptide, and/or compound of the invention in the kit for identifying, diagnosing or alleviating or treating the various diseases or disorders recited herein. Optionally, or alternately, the instructional material may describe one or more methods of identifying, diagnosing or alleviating the diseases or disorders in a cell or a tissue of a subject. The instructional material of the kit may, for example, be affixed to a container that contains one or more components of the invention or be shipped together with a container that contains the one or more components of the invention. Alternatively, the instructional material may be shipped separately from the container with the intention that the recipient uses the instructional material and the components cooperatively.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "label" when used herein refers to a detectable compound or composition that is conjugated directly or indirectly to a probe to generate a "labeled" probe. The label may be detectable by itself (e.g., radioisotope labels or fluorescent labels) or, in the case of an enzymatic label, may catalyze chemical alteration of a substrate compound or composition that is detectable (e.g., avidin-biotin). In some instances, primers can be labeled to detect a PCR product.

Assays for amplification of the known sequence are also disclosed. For example, primers for PCR may be designed to amplify regions of the sequence. For RNA, a first reverse transcriptase step may be used to generate double stranded DNA from the single stranded RNA. The array may be designed to detect sequences from an entire genome; or one or more regions of a genome, for example, selected regions of a genome, such as those coding for a protein or RNA of interest; or a conserved region from multiple genomes; or multiple genomes.

The term "amplification" refers to the operation by which the number of copies of a target nucleotide sequence present in a sample is multiplied.

As used herein, an "immunoassay" refers to any binding assay that uses an antibody capable of binding specifically to a target molecule to detect and quantify the target molecule.

The term "specifically binds", as used herein with respect to an antibody, is meant for an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

A "nucleic acid" refers to a polynucleotide and includes poly-ribonucleotides and poly-deoxyribonucleotides. Nucleic acids according to the present invention may include any polymer or oligomer of pyrimidine and purine bases, preferably cytosine, thymine, and uracil, adenine, and guanine, respectively. Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

As used herein, the term "polymerase chain reaction" ("PCR") refers to the method of K. B. Mullis, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers are then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified". As used herein, the terms "PCR product", "PCR fragment", "amplification product", or "amplicon" refer to the resultant mixture of compounds after two or more cycles of the PCR steps of denaturation, annealing and extension are complete. These terms encompass the case where there has been amplification of one or more segments of one or more target sequences.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences.

As used herein, the terms "peptide", "polypeptide", and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or any combination thereof.

As used herein, "polynucleotide" includes cDNA, RNA, DNA/RNA hybrid, antisense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, contemplated are alterations of a wild type or synthetic gene, including but not limited to deletion, insertion, substitution of one or more nucleotides, or fusion to other polynucleotide sequences.

The term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

The present invention is based in part on the discovery that the development and progression of infectious diseases or disorders is associated with an increased inosine level or activity, an increased 3-phosphoglyceric acid level or activity, an increased cGMP level or activity, a decreased phenylacetic acid level or activity, a decreased amino valerate level or activity, a decreased glycocyamine level or activity, a decreased tryptamine level or activity, a decreased gentisic acid level or activity, a decreased p-coumaric acid level or activity, a decreased N,N'-dicyclohexylurea level or activity, a decreased F16BP level or activity, a decreased tetracaine level or activity, and any combination thereof, in a subject. Thus, the invention relates to compositions and methods relating to biomarkers that can be used for identifying, diagnosing, assessing the prognosis, or assessing the effectiveness of a treatment of infectious diseases or disorders in a subject.

Methods of Diagnosing and Assessing the Prognosis

In one aspect, the present invention provides a method for diagnosing or assessing the prognosis of an infectious disease or disorder in a subject. In one aspect, the present invention also provides methods for distinguishing a subject with an infectious disease or disorder from a subject without infectious disease or disorder. In one aspect, the present invention further provides methods relating to the biomarkers of the invention that can be used to establish and evaluate treatment plans for a subject with an infectious disease or disorder.

In one embodiment, the method comprises obtaining a biological sample from a test subject. In one embodiment, the method comprises analyzing the biological sample with an assay that specifically detects at least one biomarker. In one embodiment, the method comprises detecting the level of the at least one biomarker in the biological sample of the subject. In one embodiment, the method comprises comparing the level of the at least one biomarker in the biological sample to a comparator. In one embodiment, the method comprises determining that the subject has an infectious disease or disorder when the at least one biomarker is differentially expressed in the biological sample as compared to the comparator. In one embodiment, the method comprises administering a treatment of the infectious disease or disorder to the subject.

In one embodiment, the method comprises at least one biomarker. In one embodiment, the method comprises one or more biomarkers. In one embodiment, the method comprises two or more biomarkers. In one embodiment, the method comprises three or more biomarkers. In one embodiment, the method comprises four or more biomarkers. In one embodiment, the method comprises five or more biomarkers. In one embodiment, the method comprises six or more biomarkers. In one embodiment, the method comprises seven or more biomarkers. In one embodiment, the method comprises eight or more biomarkers. In one embodiment, the method comprises nine or more biomarkers. In one embodiment, the method comprises ten or more biomarkers. In one embodiment, the method comprises eleven or more biomarkers. In one embodiment, the method comprises twelve or more biomarkers. In one embodiment, the method comprises thirteen or more biomarkers. In one embodiment, the method comprises fourteen or more biomarkers. In one embodiment, the method comprises fifteen or more biomarkers. In one embodiment, the method comprises sixteen or more biomarkers. In one embodiment, the method comprises seventeen or more biomarkers. In one embodiment, the method comprises eighteen or more biomarkers. In one embodiment, the method comprises nineteen or more biomarkers. In one embodiment, the method comprises twenty or more biomarkers.

In one embodiment, the invention is at least one biomarker for identification, diagnosis, assessment of prognosis, or treatment evaluation of infectious disease or disorder in a subject. In one embodiment, the biomarker is inosine. In one embodiment, the biomarker is 3-phosphoglyceric acid. In one embodiment, the biomarker is cGMP. In one embodiment, the biomarker is phenylacetic acid. In one embodiment, the biomarker is amino valerate. In one embodiment, the biomarker is glycocyamine. In one embodiment, the biomarker is tryptamine. In one embodiment, the biomarker is gentisic acid. In one embodiment, the biomarker is p-coumaric acid. In one embodiment, the biomarker is N,N'-dicyclohexylurea. In one embodiment, the biomarker is F16BP. In one embodiment, the biomarker is tetracaine. In some embodiments, the biomarker is any combination of inosine, 3-phosphoglyceric acid, cGMP, phenylacetic acid, amino valerate, glycocyamine, tryptamine, gentisic acid, p-coumaric acid, N,N'-dicyclohexylurea, F16BP, and/or tetracaine. In one embodiment, the invention provides a set or panel of biomarkers for identification, diagnosis, assessment of prognosis, or treatment evaluation of infectious disease or disorder in a subject, wherein the set of biomarkers comprises two or more of inosine, 3-phosphoglyceric acid, cGMP, phenylacetic acid, amino valerate, glycocyamine, tryptamine, gentisic acid, p-coumaric acid, N,N'-dicyclohexylurea, F16BP, and tetracaine.

In certain embodiments, the method comprises determining if the level of the relevant biomarkers is differentially expressed as compared to a comparator. In certain embodiments, the comparator may be the level (e.g., activity, amount, concentration, concentration of the ionized form, concentration of the neutral form, expression, level, etc.) of the relevant biomarkers in a subject not having an infectious disease or disorder, a population not having an infectious disease or disorder, or a combination thereof. In certain embodiments, the method comprises determining if the levels of the relevant biomarkers in a sample obtained from the subject are differentially expressed as compared to the levels of the relevant biomarkers in a subject and/or population where an infectious disease or disorder has not recurred. In various embodiments, the subject is a human subject, and may be of any race, ethnicity, sex, and age.

In various embodiments, the comparator is the level (e.g., activity, amount, concentration, concentration of the ionized form, concentration of the neutral form, expression, level, etc.) of the relevant biomarkers in a biological sample obtained from a human subject, an average of multiple human subjects, an average of multiple human subjects living in the same region, an average of multiple human subjects with the same age, an average of multiple human subjects with the same race, an average of multiple human subjects with the same ethnicity, an average of multiple human subjects with the same sex, an average of multiple human subjects living in different regions, an average of multiple human subjects with different ages, an average of multiple human subjects with different races, an average of multiple human subjects with different ethnicities, an average of multiple human subjects with different sexes, or any combination thereof.

In one embodiment, the method comprises detecting the level of at least one biomarker in a biological sample obtained from the subject, wherein the at least one biomarker is selected from the group consisting of inosine, 3-phosphoglyceric acid, cGMP, phenylacetic acid, amino valerate, glycocyamine, tryptamine, gentisic acid, p-coumaric acid, N,N'-dicyclohexylurea, F16BP, and tetracaine; comparing the level of the at least one biomarker in the biological sample to a comparator; and determining that the subject has an infectious disease or disorder when the at least one biomarker is differentially expressed in the biological sample as compared to the comparator.

In one embodiment, a subject is identified as having an infectious disease or disorder when the level of inosine is increased in the biological sample as compared to a comparator. In one embodiment, a subject is identified as having an infectious disease or disorder when the level of 3-phosphoglyceric acid is increased in the biological sample as compared to a comparator. In one embodiment, a subject is identified as having an infectious disease or disorder when the level of cGMP is increased in the biological sample as compared to a comparator. In one embodiment, a subject is identified as having an infectious disease or disorder when the level of phenylacetic acid is decreased in the biological sample as compared to a comparator. In one embodiment, a subject is identified as having an infectious disease or disorder when the level of amino valerate is decreased in the biological sample as compared to a comparator. In one embodiment, a subject is identified as having an infectious disease or disorder when the level of glycocyamine is decreased in the biological sample as compared to a comparator. In one embodiment, a subject is identified as having an infectious disease or disorder when the level of tryptamine is decreased in the biological sample as compared to a comparator. In one embodiment, a subject is identified as having an infectious disease or disorder when the level of gentisic acid is decreased in the biological sample as compared to a comparator. In one embodiment, a subject is identified as having an infectious disease or disorder when the level of p-coumaric acid is decreased in the biological sample as compared to a comparator. In one embodiment, a subject is identified as having an infectious disease or disorder when the level of N,N'-dicyclohexylurea is decreased in the biological sample as compared to a comparator. In one embodiment, a subject is identified as having an infectious disease or disorder when the level of F16BP is decreased in the biological sample as compared to a comparator. In one embodiment, a subject is identified as having an infectious disease or disorder when the level of tetracaine is decreased in the biological sample as compared to a comparator. In one embodiment, a subject is identified as having an infectious disease or disorder when the level of inosine is increased, the level of 3-phosphoglyceric acid is increased, the level of cGMP in increased, the level of phenylacetic acid is decreased, the level of amino valerate is decreased, the level of glycocyamine is decreased, the level of tryptamine is decreased, the level of gentisic acid is decreased, the level of p-coumaric acid is decreased, the level of N,N'-dicyclohexylurea is decreased, the level of F16BP is decreased, the level of tetracaine is decreased, or any combination thereof, in the biological sample as compared to a comparator.

In various embodiments of the methods of the invention, the level (e.g., activity, amount, concentration, concentration of the ionized form, concentration of the neutral form, expression, level, etc.) of inosine, 3-phosphoglyceric acid, cGMP, or any combination thereof, is determined to be increased when the level of inosine, 3-phosphoglyceric acid, cGMP, or any combination thereof, in the biological sample is increased by at least 1%, by at least 5%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared to a comparator.

In various embodiments of the methods of the invention, the level (e.g., activity, amount, concentration, concentration of the ionized form, concentration of the neutral form, expression, level, etc.) of inosine, 3-phosphoglyceric acid, cGMP, or any combination thereof, is determined to be increased when the level of inosine, 3-phosphoglyceric acid, cGMP, or any combination thereof, in the biological sample is increased by at least 0.01 fold, at least 0.05 fold, at least 0.07 fold, at least 0.076 fold, at least 0.1 fold, at least 0.18 fold, at least 0.19 fold, at least 0.3 fold, at least 0.36 fold, at least 0.37 fold, at least 0.38 fold, at least 0.4 fold, at least 0.43 fold, at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 16 fold, at least 16.3 fold, at least 16.31 fold, at least 20 fold, at least 25 fold, at least 26 fold, at least 26.7 fold, at least 26.72 fold, at least 30 fold, at least 40 fold, at least 50 fold, at least 75 fold, at least 100 fold, at least 192 fold, at least 192.4 fold, at least 192.44 fold, at least 200 fold, at least 250 fold, at least 500 fold, or at least 1000 fold, or at least 10000 fold, when compared to a comparator.

In one embodiment, a subject is identified as having an infectious disease or disorder when the expression level of inosine, 3-phosphoglyceric acid, cGMP, or any combination thereof, is increased in the biological sample as compared to a comparator. For example, in some embodiments, a subject is identified as having an infectious disease or disorder when the level of inosine is increased by at least 16 fold, at least 16.3 fold, or at least 16.31 fold. In some embodiments, a subject is identified as having an infectious disease or disorder when the level of inosine is increased in a range from 16 fold to 10,000 fold. In some embodiments, a subject is identified as having an infectious disease or disorder when the level of 3-phosphoglyceric acid is increased by at least 26 fold, at least 26.7 fold, or at least 26.72 fold. In some embodiments, a subject is identified as having an infectious disease or disorder when the level of 3-phosphoglyceric acid is increased in a range from 26 fold to 10,000 fold. In some embodiments, a subject is identified as having an infectious disease or disorder when the level of cGMP is increased by at least 192 fold, at least 192.4 fold, or at least 192.44 fold. In some embodiments, a subject is identified as having an infectious disease or disorder when the level of cGMP is increased in a range from 192 fold to 10,000 fold. In some embodiments, a subject is identified as having an infectious disease or disorder when the level of at least 1, 2, or all 3 of inosine, 3-phosphoglyceric acid, cGMP in the biological sample is increased by at least 0.01 fold, at least 0.05 fold, at least 0.07 fold, at least 0.076 fold, at least 0.1 fold, at least 0.18 fold, at least 0.19 fold, at least 0.3 fold, at least 0.36 fold, at least 0.37 fold, at least 0.38 fold, at least 0.4 fold, at least 0.43 fold, at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 16 fold, at least 16.3 fold, at least 16.31 fold, at least 20 fold, at least 25 fold, at least 26 fold, at least 26.7 fold, at least 26.72 fold, at least 30 fold, at least 40 fold, at least 50 fold, at least 75 fold, at least 100 fold, at least 192 fold, at least 192.4 fold, at least 192.44 fold, at least 200 fold, at least 250 fold, at least 500 fold, or at least 1000 fold, or at least 10000 fold, when compared to a comparator.

In various embodiments of the methods of the invention, the level (e.g., activity, amount, concentration, concentration of the ionized form, concentration of the neutral form, expression, level, etc.) of phenylacetic acid, amino valerate, glycocyamine, tryptamine, gentisic acid, p-coumaric acid, N,N'-dicyclohexylurea, F16BP, tetracaine, or any combination thereof, is determined to be decreased when the level of phenylacetic acid, amino valerate, glycocyamine, tryptamine, gentisic acid, p-coumaric acid, N,N'-dicyclohexylurea, F16BP, tetracaine, or any combination thereof, in the biological sample is decreased by at least 1%, by at least 5%, by at least 10%, by at least 20%, by at least 30%, by at least 40%, by at least 50%, by at least 60%, by at least 70%, by at least 80%, by at least 90%, by at least 100%, by at least 125%, by at least 150%, by at least 175%, by at least 200%, by at least 250%, by at least 300%, by at least 400%, by at least 500%, by at least 600%, by at least 700%, by at least 800%, by at least 900%, by at least 1000%, by at least 1500%, by at least 2000%, by at least 2500%, by at least 3000%, by at least 4000%, or by at least 5000%, when compared to a comparator.

In various embodiments of the methods of the invention, the level (e.g., activity, amount, concentration, concentration of the ionized form, concentration of the neutral form, expression, level, etc.) of phenylacetic acid, amino valerate, glycocyamine, tryptamine, gentisic acid, p-coumaric acid, N,N'-dicyclohexylurea, F16BP, tetracaine, or any combination thereof, is determined to be decreased when the level of phenylacetic acid, amino valerate, glycocyamine, tryptamine, gentisic acid, p-coumaric acid, N,N'-dicyclohexylurea, F16BP, tetracaine, or any combination thereof, in the biological sample is determined to be changed by at least 0.01 fold, at least 0.05 fold, at least 0.07 fold, at least 0.076 fold, at least 0.1 fold, at least 0.18 fold, at least 0.19 fold, at least 0.3 fold, at least 0.36 fold, at least 0.37 fold, at least 0.38 fold, at least 0.4 fold, at least 0.43 fold, at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 16 fold, at least 16.3 fold, at least 16.31 fold, at least 20 fold, at least 25 fold, at least 26 fold, at least 26.7 fold, at least 26.72 fold, at least 30 fold, at least 40 fold, at least 50 fold, at least 75 fold, at least 100 fold, at least 192 fold, at least 192.4 fold, at least 192.44 fold, at least 200 fold, at least 250 fold, at least 500 fold, or at least 1000 fold, or at least 10000 fold, when compared to a comparator.

In one embodiment, a subject is identified as having an infectious disease or disorder when the expression level of phenylacetic acid, amino valerate, glycocyamine, tryptamine, gentisic acid, p-coumaric acid, N,N'-dicyclohexylurea, F16BP, tetracaine, or any combination thereof, is decreased in the biological sample as compared to a comparator. For example, in some embodiments, a subject is identified as having an infectious disease or disorder when the level of phenylacetic acid is decreased by at least 0.1 fold, or at least 0.18 fold. In some embodiments, a subject is identified as having an infectious disease or disorder when the level of phenylacetic acid is decreased in a range from 0.1 fold to 10,000 fold. In some embodiments, a subject is identified as having an infectious disease or disorder when the level of amino valerate is decreased by at least 0.3 fold, or at least 0.38 fold. In some embodiments, a subject is identified as having an infectious disease or disorder when the level of amino valerate is decreased in a range from 0.3 fold to 10,000 fold. In some embodiments, a subject is identified as having an infectious disease or disorder when the level of glycocyamine is decreased by at least 0.3 fold, or at least 0.37 fold. In some embodiments, a subject is identified as having an infectious disease or disorder when the level of glycocyamine is decreased in a range from 0.3 fold to 10,000 fold. In some embodiments, a subject is identified as having an infectious disease or disorder when the level of tryptamine is decreased by at least 0.07 fold, or at least 0.076 fold. In some embodiments, a subject is identified as having an infectious disease or disorder when the level of tryptamine is decreased in a range from 0.07 fold to 10,000 fold. In some embodiments, a subject is identified as having an infectious disease or disorder when the level of gentisic acid is decreased by at least 0.1 fold, or at least 0.19 fold. In some embodiments, a subject is identified as having an infectious disease or disorder when the level of gentisic acid is decreased in a range from 0.1 fold to 10,000 fold. In some embodiments, a subject is identified as having an infectious disease or disorder when the level of p-coumaric acid is decreased by at least 0.1 fold, or at least 0.19 fold. In some embodiments, a subject is identified as having an infectious disease or disorder when the level of p-coumaric acid is decreased in a range from 0.1 fold to 10,000 fold. In some embodiments, a subject is identified as having an infectious disease or disorder when the level of N,N'-dicyclohexylurea is decreased by at least 0.4 fold, or at least 0.43 fold. In some embodiments, a subject is identified as having an infectious disease or disorder when the level of N,N'-dicyclohexylurea is decreased in a range from 0.4 fold to 10,000 fold. In some embodiments, a subject is identified as having an infectious disease or disorder when the level of F16BP is decreased by at least 0.4 fold, or at least 0.40 fold. In some embodiments, a subject is identified as having an infectious disease or disorder when the level of F16BP is decreased in a range from 0.4 fold to 10,000 fold. In some embodiments, a subject is identified as having an infectious disease or disorder when the level of tetracaine is decreased by at least 0.3 fold, or at least 0.36 fold. In some embodiments, a subject is identified as having an infectious disease or disorder when the level of tetracaine is decreased in a range from 0.3 fold to 10,000 fold.

In some embodiments, a subject is identified as having an infectious disease or disorder when the level of 1, 2, 3, 4, 5, 6, 7, 8, or all 9 of phenylacetic acid, amino valerate, glycocyamine, tryptamine, gentisic acid, p-coumaric acid, N,N'-dicyclohexylurea, F16BP, tetracaine, or any combination thereof, is decreased by at least 0.01 fold, at least 0.05 fold, at least 0.07 fold, at least 0.076 fold, at least 0.1 fold, at least 0.18 fold, at least 0.19 fold, at least 0.3 fold, at least 0.36 fold, at least 0.37 fold, at least 0.38 fold, at least 0.4 fold, at least 0.43 fold, at least 1 fold, at least 1.1 fold, at least 1.2 fold, at least 1.3 fold, at least 1.4 fold, at least 1.5 fold, at least 1.6 fold, at least 1.7 fold, at least 1.8 fold, at least 1.9 fold, at least 2 fold, at least 2.1 fold, at least 2.2 fold, at least 2.3 fold, at least 2.4 fold, at least 2.5 fold, at least 2.6 fold, at least 2.7 fold, at least 2.8 fold, at least 2.9 fold, at least 3 fold, at least 3.5 fold, at least 4 fold, at least 4.5 fold, at least 5 fold, at least 5.5 fold, at least 6 fold, at least 6.5 fold, at least 7 fold, at least 7.5 fold, at least 8 fold, at least 8.5 fold, at least 9 fold, at least 9.5 fold, at least 10 fold, at least 11 fold, at least 12 fold, at least 13 fold, at least 14 fold, at least 15 fold, at least 16 fold, at least 16.3 fold, at least 16.31 fold, at least 20 fold, at least 25 fold, at least 26 fold, at least 26.7 fold, at least 26.72 fold, at least 30 fold, at least 40 fold, at least 50 fold, at least 75 fold, at least 100 fold, at least 192 fold, at least 192.4 fold, at least 192.44 fold, at least 200 fold, at least 250 fold, at least 500 fold, or at least 1000 fold, or at least 10000 fold, when compared to a comparator.

In some embodiments, the infectious disease or disorder is an infectious disease or disorder associated with an increased inosine level or activity, an increased 3-phosphoglyceric acid level or activity, an increased cGMP level or activity, a decreased phenylacetic acid level or activity, a decreased amino valerate level or activity, a decreased glycocyamine level or activity, a decreased tryptamine level or activity, a decreased gentisic acid level or activity, a decreased p-coumaric acid level or activity, a decreased N,N'-dicyclohexylurea level or activity, a decreased F16BP level or activity, a decreased tetracaine level or activity, and any combination thereof in a subject. In some embodiments, the infectious disease or disorder is a bacterial infection, a fungal infection, a parasitic infection, a viral infection, or a combination thereof. Examples of infectious diseases or disorders include but are not limited to Coccidioidomycosis (Valley fever), athlete's foot, ringworm, fungal eye infection, rhinovirus, coronavirus, adenovirus, encephalitis, meningitis, enterovirus infection, herpes infection, warts, skin infection, human papillomaviruses (HPV) infection, herpes simplex virus (HSV) infection, gastroenteritis, norovirus infection, Zika virus infection, human immunodeficiency virus (HIV) infection, hepatitis C, polio, influenza, Dengue fever, H1N1 swine flu, Ebola, Middle East respiratory syndrome (MERS-COV), cocci infection, bacilli infection, spirochetes infection, cholera, diphtheria, dysentery, bubonic plague, pneumonia, tuberculosis, typhoid, typhus, bacterial meningitis, otitis media, upper respiratory tract infection, gastritis, food poisoning, eye infection, bacterial eye infection, sinusitis, urinary tract infection, sexually transmitted diseases, protozoan infection, amebic dysentery, helminth infection, flatworms, roundworms, ectoparasitic infection, and infection caused by mites, ticks, lice, fleas, and/or mosquitos.

In one aspect, the present invention relates to a method of distinguishing between a subject with an infectious disease or disorder and a subject without an infectious disease or disorder. In one aspect, the present invention relates to a method of distinguishing between different types of infectious diseases or disorders. In one embodiment, the method distinguishes between subjects with different types of infectious diseases or disorders. In one embodiment, the method distinguishes between a subject with a fungal infection and a subject with a bacterial infection. In one embodiment, the method distinguishes between a subject with a fungal infection and a subject with a parasitic infection. In one embodiment, the method distinguishes between a subject with a fungal infection and a subject with a viral infection. In one embodiment, the method distinguishes between a subject with a bacterial infection and a subject with a parasitic infection. In one embodiment, the method distinguishes between a subject with a bacterial infection and a subject with a viral infection. In one embodiment, the method distinguishes between a subject with a parasitic infection and a subject with a viral infection.

In some methods of the invention, a biological sample from a subject is assessed for the level of one or more of the markers of the invention in the biological sample obtained from the patient. The level of one or more of the markers of the invention in the biological sample can be determined by assessing the amount of one or more of the biomarkers of the invention in the biological sample, the amount of activity of one or more of the biomarkers of the invention in the biological sample, the amount of concentration of one or more of the biomarkers of the invention in the biological sample, the amount of one or more of the biomarkers of the invention in the biological sample, or any combination thereof.

Biological samples may be of any biological tissue or fluid. Frequently the sample will be a "clinical sample" which is a sample derived from a patient. The biological sample may contain any biological material suitable for detecting the desired biomarkers, and may comprise cellular and/or non-cellular material obtained from the individual. A biological sample can be obtained by appropriate methods, such as, by way of examples, blood draw, fluid draw, biopsy, or surgical resection. Examples of biological samples include but are not limited to blood, lymph, urine, saliva, mucus, plasma, biological tissue, feces, gastrointestinal fluid, semen, and biopsies. Samples that are liquid in nature are referred to herein as "bodily fluids". Body samples may be obtained from a patient by a variety of techniques including, for example, by scraping or swabbing an area or by using a needle to aspirate bodily fluids. Methods for collecting various body samples are well known in the art. Frequently, a sample will be a "clinical sample", i.e., a sample derived from a patient. Such samples include, but are not limited to, bodily fluids which may or may not contain cells, e.g., blood (e.g., whole blood, serum or plasma), urine, saliva, tissue or fine needle biopsy samples, tissue sample obtained during surgical resection, and archival samples with known diagnosis, treatment, and/or outcome history. In some embodiments, the biological sample comprises a biological tissue of the subject, a blood sample of the subject, a bodily fluid sample of the subject, a fecal sample of the subject, a plasma sample of the subject, a saliva sample of the subject, a urine sample of the subject, or any combination thereof.

In one embodiment, the method comprises analyzing the biological sample with an assay that specifically detects a biomarker. In one embodiment, the method comprises analyzing the biological sample with an assay that specifically detects at least one biomarker. Examples of such assay include, but are not limited to: mass spectrometry (MS), liquid chromatography (LC), liquid chromatography-mass spectrometry (LC-MS), targeted liquid chromatography-tandem mass spectrometry (LC-MS/MS), high-performance liquid chromatography (HPLC), ultra-performance liquid chromatography (UPLC), ultra-high-performance liquid chromatography (UHPLC), gas chromatography (GC), gas chromatography-mass spectrometry (GC-MS), globally optimized targeted mass spectrometry, targeted assay of about 200 metabolites, aqueous global profiling, liquid global profiling, GC-MS profiling, GC-MS flux analysis, carnitine analysis, lipid targeted analysis, quantitative lipid targeted analysis, tryptophan analysis, absolute quantification, multivariate statistical analysis, dynamic light scattering (DLS), nuclear magnetic resonance (NMR) spectroscopy, ultraviolet-visible (UV/Vis) spectroscopy, infrared (IR) spectroscopy, Raman spectroscopy, or any combination thereof.

In one embodiment, the method comprises using a multidimensional non-linear algorithm to determine if the level (e.g., activity, amount, concentration, concentration of the ionized form, concentration of the neutral form, expression, level, etc.) of a set of biomarkers in the biological sample is statistically different than a comparator. In some embodiments, the algorithm is drawn from the group consisting essentially of: linear or nonlinear regression algorithms; linear or nonlinear classification algorithms; ANOVA; neural network algorithms; genetic algorithms; support vector machines algorithms; hierarchical analysis or clustering algorithms; hierarchical algorithms using decision trees; kernel based machine algorithms such as kernel partial least squares algorithms, kernel matching pursuit algorithms, kernel fisher discriminate analysis algorithms, or kernel principal components analysis algorithms; Bayesian probability function algorithms; Markov Blanket algorithms; a plurality of algorithms arranged in a committee network; and forward floating search or backward floating search algorithms.

In one embodiment, the method comprises detecting one or more biomarkers in a biological sample of the subject. In some embodiments, the level of one or more of markers of the invention in the biological test sample of the subject is compared to a comparator. Non-limiting examples of comparators include, but are not limited to, a negative control, a positive control, standard control, standard value, an expected normal background value of the subject, a historical normal background value of the subject, a reference standard, a reference level, an expected normal background value of a population that the subject is a member of, or a historical normal background value of a population that the subject is a member of. In one embodiment, the comparator is a level (e.g., activity, amount, concentration, concentration of the ionized form, concentration of the neutral form, expression, level, etc.) of the one or more biomarker in a sample obtained from a subject not having an infectious disease or disorder. In one embodiment, the comparator is a level of the one or more biomarker in a sample obtained from a subject known not to have an infectious disease or disorder.

In one embodiment, the comparator is a level of the one or more biomarker in a sample obtained from a subject having a different infectious disease or disorder (e.g. fungal infection vs bacterial infection, fungal infection vs parasitic infection, fungal infection vs viral infection, bacterial infection vs parasitic infection, bacterial infection vs viral infection, parasitic infection vs viral infection, etc.). In one embodiment, the comparator is a level of the one or more biomarker in a sample obtained from a subject known to have a different infectious disease or disorder (e.g. fungal infection vs bacterial infection, fungal infection vs parasitic infection, fungal infection vs viral infection, bacterial infection vs parasitic infection, bacterial infection vs viral infection, parasitic infection vs viral infection, etc.).

In one aspect, the present invention includes methods for identifying subjects who have an infectious disease or disorder and subjects who do not have an infectious disease or disorder by detection of the biomarkers disclosed herein. In some embodiments, the biomarkers are used to generate a biomarker profile or signature of the subjects: (i) who have an infectious disease or disorder, and/or (ii) who do not have an infectious disease or disorder. In some embodiments, the biomarkers are used to generate a biomarker profile or signature of the subjects: (i) who have an infectious disease or disorder associated with fungal infection, (ii) who have an infectious disease or disorder associated with bacterial infection, (iii) who have an infectious disease or disorder associated with parasitic infection, (iv) who have an infectious disease or disorder associated with viral infection, (v) who do not have an infectious disease or disorder associated with fungal infection, (vi) who do not have an infectious disease or disorder associated with bacterial infection, (vii) who do not have an infectious disease or disorder associated with parasitic infection, (viii) who do not have an infectious disease or disorder associated with viral infection, or any combination thereof.

In one embodiment, the biomarker profile of a subject is compared to a predetermined or comparator biomarker profile or reference biomarker profile to identify an infectious disease or disorder. In one embodiment, the biomarker profile of a subject is compared to a predetermined or comparator biomarker profile or reference biomarker profile to diagnose an infectious disease or disorder. In one embodiment, the biomarker profile of a subject is compared to a predetermined or comparator biomarker profile or reference biomarker profile to assess the prognosis of an infectious disease or disorder. In one embodiment, the biomarker profile of a subject is compared to a predetermined or comparator biomarker profile or reference biomarker profile to evaluate the treatment of an infectious disease or disorder. In one embodiment, the biomarker profile of a subject is compared to a predetermined or comparator biomarker profile or reference biomarker profile to distinguish between different types of infectious diseases or disorders.

Control group samples may either be from a normal subject, samples from subjects with a known diagnosis of an infectious disease or disorder, or samples from subjects with no known diagnosis of an infection disease or disorder. As described below, comparison of the expression patterns of the sample to be tested with comparators can be used to identify or diagnose an infectious disease or disorder in the subject. In some instances, the control groups are only for the purposes of establishing initial cutoffs or thresholds for the assays of the invention. Therefore, in some instances, the systems and methods of the invention can identify or diagnose an infectious disease or disorder without the need to compare with a control group.

Information obtained from the methods of the invention described herein can be used alone, or in combination with other information (e.g., age, family history, disease status, disease history, vital signs, blood chemistry, PSA level, Gleason score, lymph node staging, metastasis staging, expression of other gene signatures relevant to outcomes of an infectious disease or disorder, etc.) from the subject or from the biological sample obtained from the subject. In some embodiments, the biomarkers data is combined or correlated with other data or test results that include, but are not limited to measurements or results from serologic testing methods, enzyme immunoassay (EIA), complement fixation (CF), immunodiffusion, clinical presentation, serology, radiography, histology, culture, and clinical parameters or other algorithms for developing or having an infectious disease or disorder. In one embodiment, data include, but are not limited to age, ethnicity, PSA level, Gleason score, lymph node staging, metastasis staging, and other genomic data, and specific expression values of other gene signatures relevant to infection outcomes. In one embodiment, the data comprises subject information, such as medical history, travel history, and/or any relevant family history. Several serology techniques that can be used in combination with the compositions and methods of the present invention. Examples of serology techniques include, but are not limited to: ELISA, agglutination, precipitation, complement-fixation, fluorescent antibodies, and chemiluminescence.

In certain embodiments, the method comprises using surgical data in combination with the detection of the relevant biomarkers described herein to diagnose, assess the prognosis, or assess the effectiveness of a treatment of an infectious disease or disorder. For example, in certain embodiments, the method comprises assessing the severity of an infectious disease or disorder, the spread of an infectious disease or disorder to the lymph node (N category), or spread of an infectious disease or disorder to other parts of the body (metastatic stage) (M category).

In one aspect, the invention contemplates the detection of differentially expressed biomarkers using tissue microarray. In one embodiment, the method comprises diagnosing an infectious disease or disorder by detecting differentially expressed biomarkers in biological tissue excised from the subject during biopsy. In one aspect, the invention further contemplates using methods known to those skilled in the art to detect and to measure the level of one or more differentially expressed marker expression products.

In one embodiment, a cellular or fluid examination is used to detect or measure a variety of molecules including RNA, protein, and a number of molecules that are modified as a result of the protein's function. Exemplary diagnostic methods focusing on nucleic acids include but are not limited to amplification techniques, such as PCR and RT-PCR (including quantitative variants), and hybridization techniques, such as in situ hybridization, microarrays, and blots. Exemplary diagnostic methods focusing on proteins include but are not limited to binding techniques, such as ELISA, immunohistochemistry, microarray, and functional techniques, such as enzymatic assays.

The genes identified as being differentially expressed may be assessed in a variety of nucleic acid detection assays to detect or quantify the expression level of a gene or multiple genes in a given sample. For example, traditional Northern blotting, nuclease protection, RT-PCR, microarray, and differential display methods may be used for detecting gene expression levels. Methods for assaying for mRNA include Northern blots, slot blots, dot blots, and hybridization to an ordered array of oligonucleotides. Any method for specifically and quantitatively measuring a specific protein or mRNA or DNA product can be used. However, methods and assays are most efficiently designed with array or chip hybridization-based methods for detecting the expression of a large number of genes. Any hybridization assay format may be used, including solution-based and solid support-based assay formats.

The protein products of the genes identified herein can also be assayed to determine the amount of expression. Methods for assaying for a protein include Western blot, immunoprecipitation, and radioimmunoassay. The proteins analyzed may be localized intracellularly (most commonly an application of immunohistochemistry) or extracellularly (most commonly an application of immunoassays such as ELISA).

In some embodiments, the invention relates to different types of biomarkers (e.g., protein level or activity, nucleic acid level or activity, mRNA level or activity, gene expression. etc.) and their measurements that can be combined with the compositions and methods of the present invention. In various embodiments, the neutral form of the biomarkers is measured. In various embodiments, the derivative form of the biomarkers is measured. In various embodiments, the ionized form of the biomarkers is measured. In various embodiments, measurements of neutral biomarkers are used in conjunction with measurements of ionized biomarkers. Biomarkers generally can be measured and detected through a variety of assays, methods and detection systems known to one of skill in the art. Various methods include but are not limited to immunoassays, microarray, PCR, RT-PCR, refractive index spectroscopy (RI), ultra-violet spectroscopy (UV), fluorescence analysis, electrochemical analysis, radiochemical analysis, near-infrared spectroscopy (near-IR), infrared (IR) spectroscopy, nuclear magnetic resonance spectroscopy (NMR), light scattering analysis (LS), mass spectrometry, pyrolysis mass spectrometry, nephelometry, dispersive Raman spectroscopy, gas chromatography, liquid chromatography, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, colorimetry and surface plasmon resonance. In this regard, biomarkers can be measured using the above-mentioned detection methods, or other methods known to the skilled artisan. Other biomarkers can be similarly detected using reagents that are specifically designed or tailored to detect them.

In some embodiments of the invention, methods of measuring biomarker levels in a biological sample obtained from a subject include, but are not limited to, an immunochromatography assay, an immunodot assay, a Luminex assay, an ELISA assay, an ELISPOT assay, a protein microarray assay, a ligand-receptor binding assay, displacement of a ligand from a receptor assay, displacement of a ligand from a shared receptor assay, an immunostaining assay, a Western blot assay, a mass spectrophotometry assay, a radioimmunoassay (RIA), a radioimmunodiffusion assay, a liquid chromatography-tandem mass spectrometry assay, an Ouchterlony immunodiffusion assay, reverse phase protein microarray, a rocket immunoelectrophoresis assay, an immunohistostaining assay, an immunoprecipitation assay, a complement fixation assay, FACS, an enzyme-substrate binding assay, an enzymatic assay, an enzymatic assay employing a detectable molecule, such as a chromophore, fluorophore, or radioactive substrate, a substrate binding assay employing such a substrate, a substrate displacement assay employing such a substrate, and a protein chip assay.

The concentration of the biomarker in a sample may be determined by any suitable assay. A suitable assay may include one or more of the following methods, an enzyme assay, an immunoassay, mass spectrometry, chromatography, electrophoresis or an antibody microarray, or any combination thereof. Thus, as would be understood by one skilled in the art, the systems and methods of the invention may include any method known in the art to detect a biomarker in a sample.

The invention described herein also relates to methods for a multiplex analysis platform. In one embodiment, the method comprises an analytical method for multiplexing analytical measurements of markers.

In various embodiments, the subject is a human subject, and may be of any race, ethnicity, sex, and age.

Methods of Treatment

In some embodiments, the present invention further provides methods relating to the biomarkers of the invention that can be used to establish and evaluate treatment plans for a subject with an infectious disease or disorder. In some embodiments, the invention includes methods for assessing the effectiveness of a treatment of an infectious disease or disorder by detecting differentially expressed biomarkers in a biological sample obtained from a subject. For example, in certain embodiments, the method comprises assessing the effectiveness of a treatment of an infectious disease or disorder by detecting differentially expressed biomarkers in a biological sample obtained from a subject having an infectious disease or disorder or being treated for an infectious disease or disorder.

In some embodiments of the invention, the methods comprise a) providing a biological sample from the subject; b) analyzing the biological sample with an assay that specifically detects at least one biomarker of the invention in the biological sample; c) comparing the level of the at least one biomarker in the sample to a comparator, wherein a statistically significant difference between the level of the at least one biomarker in the sample to a comparator or the level of the at least one biomarker in an earlier obtained biological sample is indicative of an infectious disease or disorder in the subject. In some embodiments, the methods further comprise the step of d) effectuating a treatment regimen based thereon.

In some embodiments, the method of treatment comprises the detection of a differential expression of one or more biomarkers that indicate a treatment of the subject is needed. In one embodiment, the treatment is determined based on the level of the at least one biomarker in a subject. In some embodiments, the method of treatment includes, but is not limited to pharmacotherapy, surgery, radiation, and chemotherapy. In some embodiments, the method of treatment comprises administering a therapeutically effective amount of a drug. Examples of such drugs include, but are not limited to: a nucleic acid, a peptide, a small molecule chemical compound, an siRNA, a ribozyme, an antisense nucleic acid, an aptamer, a peptidomimetic, an antibody, an antibody fragment, an antibiotic, antifungal medication, and a combination thereof.

In some embodiments, the method of treatment comprises monitoring the biomarker levels during the course of treatment of a disease or disorder. In some embodiments, the method of treatment comprises an assessment of the effectiveness of the treatment regimen for an infectious disease or disorder by detecting one or more biomarkers in an effective amount from samples obtained from a subject over time and comparing the amount of biomarker or biomarkers detected. In some embodiments, a first sample is obtained prior to the subject receiving treatment and one or more subsequent samples are taken after or during treatment of the subject. In some embodiments, changes in biomarker levels over time provide an indication of effectiveness of the therapy.

In one aspect, the biomarkers are used to monitor subjects undergoing treatments and therapies for an infectious disease or disorder, subjects who have had an infectious disease or disorder, and subjects who are in remission of a previously diagnosed and treated infectious disease or disorder. In one embodiment, the biomarkers are used to select or modify treatments in subjects having an infectious disease or disorder, subjects who have had an infectious disease or disorder, and subjects who are in remission of a previously diagnosed and treated infectious disease or disorder.

In some embodiments, the methods of the present invention comprise effecting a therapy and/or the treatment regime based on the diagnosis or assessment of prognosis of an infectious disease or disorder. In one embodiment, the treatment is adjusted based on the level of the at least one biomarker in a subject.

In one aspect, the present invention also provides methods for identifying agents for treating an infectious disease or disorder that are appropriate or otherwise customized for a specific subject. In one embodiment, a test sample from a subject, exposed to a therapeutic agent or a drug, can be taken and the level of one or more biomarkers can be determined. In one embodiment, the level of one or more biomarkers can be compared to a sample derived from the subject before and after treatment, or can be compared to samples derived from one or more subjects who have shown improvements or alleviation of an infectious disease or disorder as a result of such treatment or exposure.

To identify therapeutics or drugs that are appropriate for a specific subject, a test sample from the subject can also be exposed to a therapeutic agent or a drug, and the level of one or more biomarkers can be determined. Biomarker levels can be compared to a sample derived from the subject before and after treatment or exposure to a therapeutic agent or a drug, or can be compared to samples derived from one or more subjects who have shown improvements relative to a disease as a result of such treatment or exposure. Thus, in one aspect, the invention provides a method of assessing the efficacy of a therapy with respect to a subject comprising a step of taking a first measurement of a biomarker panel in a first sample from the subject; a step of effecting the therapy with respect to the subject; a step of taking a second measurement of the biomarker panel in a second sample from the subject; and a step of comparing the first and second measurements to assess the efficacy of the therapy.

Additionally, therapeutic agents suitable for administration to a particular subject can be identified by detecting one or more biomarkers in an effective amount from a sample obtained from a subject and exposing the subject-derived sample to a test that determines the amount of the biomarker(s) in the subject-derived sample. Accordingly, treatments or therapeutic regimens for use in subjects having an enhanced risk for developing an infectious disease or disorder can be selected based on the amounts of biomarkers in samples obtained from the subjects and compared to a reference value. Two or more treatments or therapeutic regimens can be evaluated in parallel to determine which treatment or therapeutic regimen would be the most efficacious for use in a subject to delay onset, or slow progression of a disease. In various embodiments, a recommendation is made on whether to initiate or continue treatment of a disease.

In various exemplary embodiments, the methods of the invention include effecting a therapy for the treatment of a diagnosed disease. In one embodiment, effecting a therapy comprises administering a disease-modulating drug to the subject. The subject may be treated with one or more drugs until altered levels of the measured biomarkers return closer to the baseline value measured in a population not having an infectious disease or disorder, not having recurrence of an infectious disease or disorder, or showing improvements in disease biomarkers as a result of treatment with a drug. Additionally, improvements related to a changed level of a biomarker or clinical parameter may be the result of treatment with a disease-modulating drug. For example, in one embodiment, effecting a therapy comprises administering an antifungal drug to a subject. Exemplary antifungal agents that can be administered include, but are not limited to, fluconazole and itraconazole.

In various embodiments, effecting a therapy comprises treatment of one or more symptoms of the disease or disorder. For example, in one embodiment, effecting a therapy comprises administration of a non-disease-modulating drug to the subject. Exemplary non-disease-modulating drugs that may be administered include, but are not limited to, pain relievers, anti-inflammatory drugs, NSAIDs, decongestants, cough suppressants, including topical cough suppressants, or other agents that may function to reduce the severity of at least one symptom of the disease or disorder.

Any drug or any combination of drugs disclosed herein may be administered to a subject to treat a disease. The drugs herein can be formulated in any number of ways, often according to various known formulations in the art or as disclosed or referenced herein.

In various embodiments, any drug or any combination of drugs disclosed herein is not administered to a subject to treat a disease. In these embodiments, the practitioner may refrain from administering the drug or any combination of drugs, may recommend that the subject not be administered the drug or any combination of drugs or may prevent the subject from being administered the drug or any combination of drugs.

In various embodiments, one or more additional drugs may be optionally administered in addition to those that are recommended or have been administered. An additional drug will typically not be any drug that is not recommended or that should be avoided.

Kits

The present invention also pertains to kits useful in the methods of the invention. Such kits comprise various combinations of components useful in any of the methods described elsewhere herein, including for example, materials for quantitatively analyzing a biomarker of the invention, materials for assessing the activity of a biomarker of the invention, and instructional material. For example, in one embodiment, the kit comprises components useful for the quantification of a desired biomarker in a biological sample. In a further embodiment, the kit comprises components useful for the assessment of the activity of a desired biomarker in a biological sample.

In a further embodiment, the kit comprises the components of an assay for monitoring the effectiveness of a treatment administered to a subject in need thereof, containing instructional material and the components for determining whether the level of a biomarker of the invention in a biological sample obtained from the subject is modulated during or after administration of the treatment. In various embodiments, to determine whether the level of a biomarker of the invention is modulated in a biological sample obtained from the subject, the level of the biomarker is compared to at least one comparator contained in the kit, such as a positive control, a negative control, a historical control, a historical norm, or the level of another reference molecule in the biological sample. In certain embodiments, the ratio of the biomarker and a reference molecule is determined to aid in the monitoring of the treatment.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Example 1: Coccidioidomycosis Detection Using Targeted Plasma and Urine Metabolic Profiling Broadly, fungal infections can induce wide and extensive alterations in metabolism, which provides a promising approach to detect fungal infections, such as VF. Fungal infections induce wide and extensive metabolic alterations and metabolic flexibility is generally essential for fungal pathogenicity. For example, fungal pathogens must assimilate local nutrients to establish an infection in their mammalian host, and metabolic flexibility is generally essential for fungal pathogenicity.

Diagnosis of VF is difficult due to (1) presentation of vague symptoms and (2) current available diagnostic techniques that are inaccurate, non-specific, time-consuming, costly, and invasive. The current diagnostic method for VF is serological testing methods. However, no single serological test exhibits high sensitivity and specificity and many patients fail to produce an immunological response. Thus, in order to achieve an accurate diagnosis, a combination of various methods (i.e., clinical presentation, serology, radiography, histology, and cultures) are necessary. However, these methods are also costly, time-consuming, invasive, etc.

Since metabolites are sensitive to subtle differences and changes in pathological status, metabolomics, the comprehensive study of small molecular-weight metabolites and their dynamic changes in biological systems, provides advanced methods to identify changing metabolite levels, and has resulted in the rapid discovery of disease biomarkers during the past decade. Mass spectrometry (MS)-based metabolic profiling has proven to be a promising tool for analyzing metabolic alterations due to various diseases and, therefore, can provide sensitive and valuable diagnostic information, pathogenesis identification, and potential therapeutic targets for clinical treatments and disease monitoring. Indeed, previous studies have used MS-based methods in conjunction with chemometric analyses to develop metabolic biomarker panels for the accurate diagnosis of fungal infections, such as mucormycosis and aspergillosis, as well as detection of various mycotoxins produced as a result of host-fungal interactions.

In the field of diagnosing VF, robust metabolic markers to enable effective screening, rapid diagnosis, accurate surveillance, and therapeutic monitoring of VF are still lacking. This example explores a faster, more accurate (higher sensitivity and specificity), cheaper, less invasive method. In this example, targeted liquid chromatography-tandem mass spectrometry (LC-MS/MS) was utilized to create a metabolic profiling approach for identifying metabolic marker candidates to aid in specific VF detection. The study in Example 1 is a first in utilizing mass spectrometry to apply metabolomics to detect VF in humans. Thus, this example represents the first targeted plasma and urine liquid chromatography-tandem mass spectrometry (LC-MS/MS) profiling approach for the rapid and accurate detection of VF (FIG. 1).

Example 1 discloses a novel approach, which utilized LC-MS/MS in the multi-step biomarker selection and metabolic profiling method in a study of 147 patients, for rapid and routine VF diagnosis with significant advantages to current diagnostic methods. This approach utilized metabolite markers that aid in higher specificity diagnosis (i.e., plasma metabolites: 97.6% and urine metabolites: 88.1%) and metabolite markers that aid in higher sensitivity diagnosis (i.e., plasma metabolites: 94.4% and urine metabolites: 89.7%) versus the current available urinary antigen tests (i.e., ~70%) to provide a faster (within 24 hours) and cost-effective approach to diagnosis.

Metabolic Profiles

A total of 48 VF patients and 99 non-VF controls were included in the study. Of the VF samples, 18 were plasma and 30 were urine (FIG. 2). Of the non-VF control samples, 41 were from plasma and 58 from urine. Paired plasma and urine samples were only obtained from one patient, although on different days, given that this was not a coordinated collection. Roughly half of all VF patients were taking antifungal medication at the time of sample collection. Table 1 shows the clinical and demographic characteristics of patients included in the study. There was no statistically significant difference in plasma or urine metabolites between VF patients on antifungal medication and those VF patients not taking antifungals, as calculated by a Mann-Whitney U test (all q>0.05).

TABLE 1

Clinical and demographic characteristics of study participants.

| | | Total | Gender | | Age | | Clinical Course of Disease | | | Serology (EIA, CF or ID) | | Antifungals? | |
|---|---|---|---|---|---|---|---|---|---|---|---|---|---|
| | | n (%) | Male | Female | <65 | ≥65 | Acute | Chronic | Disseminated | Pos. | Neg. | Yes | No |
| VF (+) | Urine | 30 (62.5) | 19 (63.3) | 11 (36.7) | 15 (50) | 15 (50) | 17 (56.7) | 10 (33.3) | 3 (10) | 24 (80) | 6 (20) | 25 (83.3) | 5 (16.7) |
| | Plasma | 18 (37.5) | 11 (61.1) | 7 (38.9) | 10 (55.6) | 8 (44.4) | 10 (55.5) | 3 (16.7) | 5 (27.8) | 16 (88.9) | 2 (11.1) | 5 (27.8) | 13 (72.2) |
| VF (−) | Urine | 58 (59) | 34 (58.6) | 24 (41.4) | 31 (53.4) | 27 (46.6) | N/A | N/A | N/A | N/A | N/A | N/A | N/A |
| | Plasma | 41 (41) | 22 (53.7) | 19 (46.3) | 29 (70.7) | 12 (29.3) | N/A | N/A | N/A | N/A | N/A | N/A | N/A |

Figure 3:
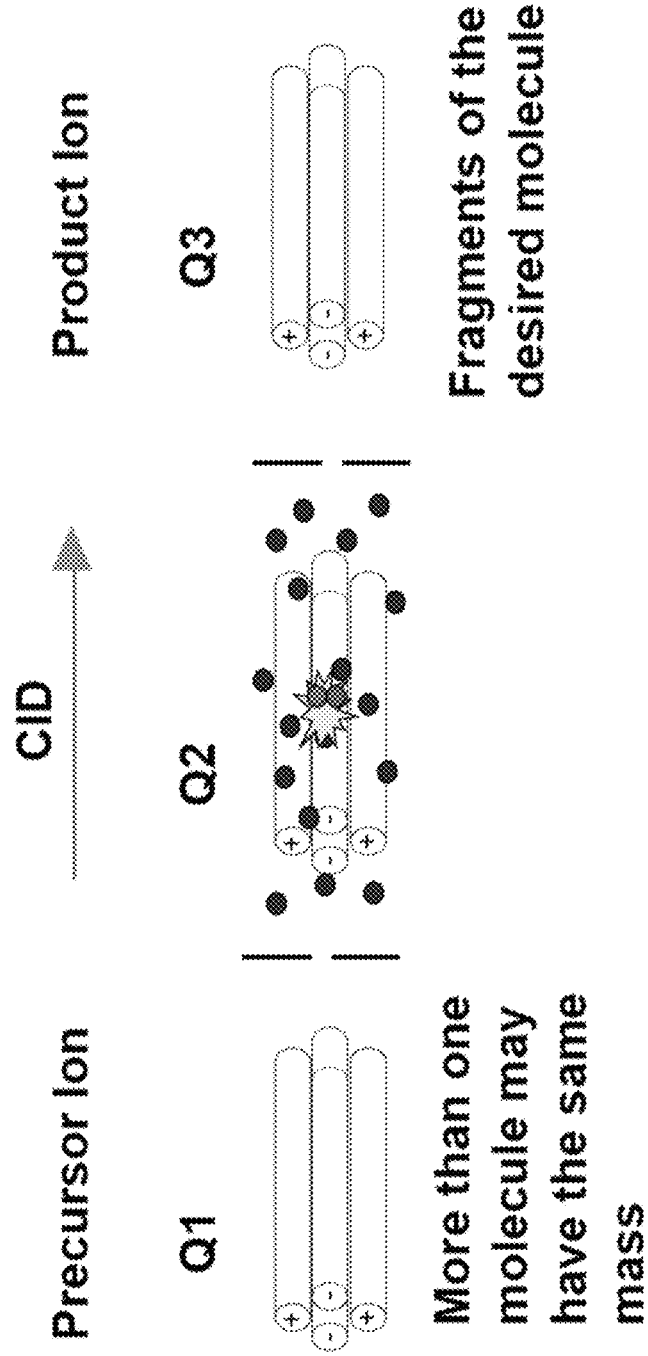
FIG. 3 depicts a schematic representation of targeted detection-triple quadrupole mass spectrometry (QQQ-MS). Combination of precursor and product ions (plus chromatography) enables high sensitivity and specificity.
Figure 4A:
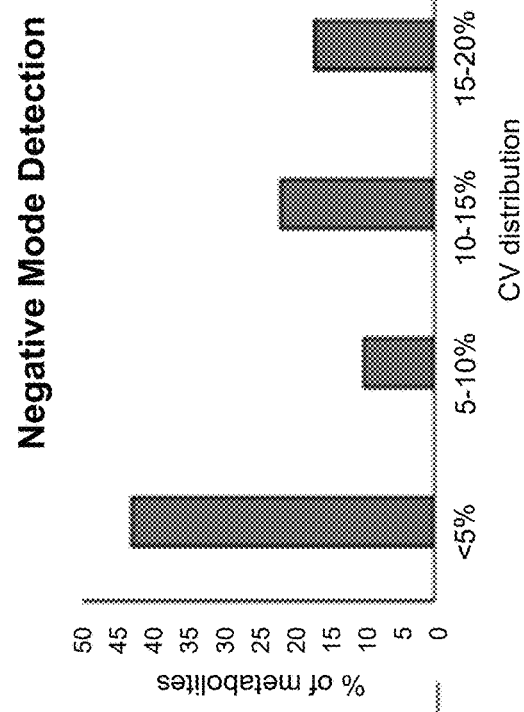
FIG. 4A through FIG. 4D, depicts results that demonstrate distribution of coefficient of variation (CV) values of measured plasma and urine metabolites (Plasma QC CV range: 0.46%-13.01%, median CV: 11.91%, with ~70% of metabolites having CV<15%; and Urine QC CV range: 0.02%-12.00%, median CV: 11.37%, with ~85% of metabolites having CV<15%).
Figure 4B:
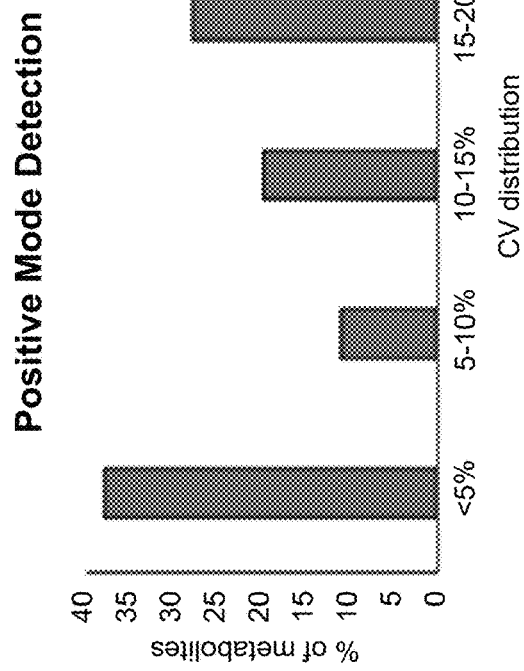
Figure 4C:
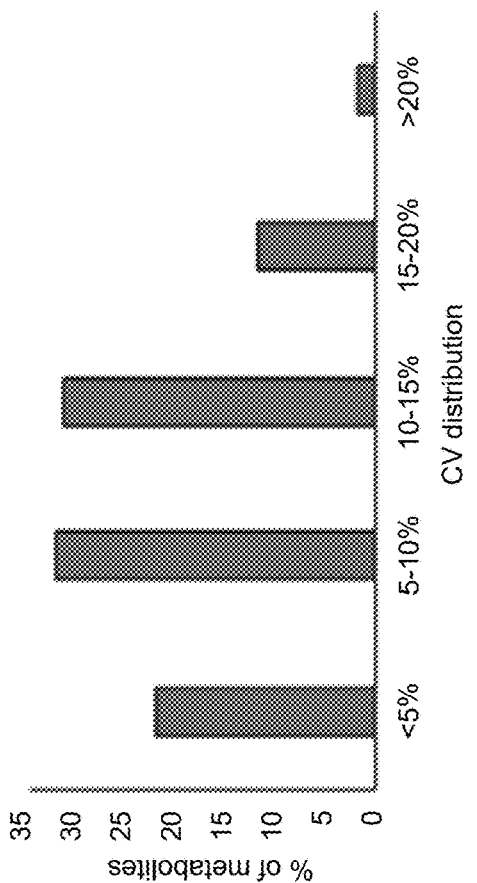
Figure 4D:
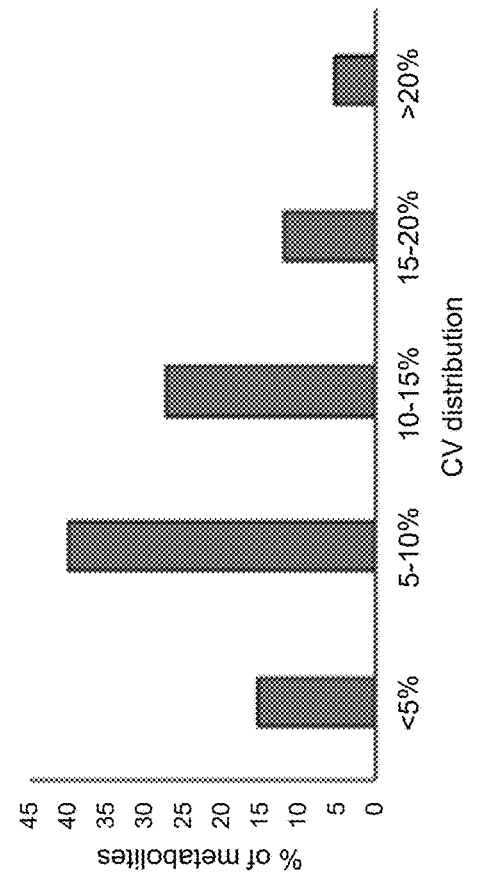

In the current study, a large-scale, targeted LC-MS/MS approach was used for reliable and comprehensive VF plasma and urine metabolic profiling (FIG. 3). Using this metabolic profiling system, targeted analysis of 278 MRM transitions was achieved for metabolites spanning over 20 different chemical classes (such as amino acids, carboxylic acids, pyridines, etc.) from more than 35 metabolic pathways (e.g., TCA cycle, amino acid metabolism, glycolysis, purine and pyrimidine metabolism, urea cycle, etc.) in both positive and negative ionization modes. In total, 207 plasma metabolites and 231 urine metabolites were found to be reliably detected with relative abundances >1,000 in more than 80% of all samples. After normalization by averaged values from QC injection data, relative levels of the 207 plasma metabolites had a median coefficient of variation (CV) value of 11.91% (range: 0.46%-13.01%) with ~70% of metabolites having CV<15%, while the 231 reliably detected urine metabolites had a median CV value of 11.37% (range: 0.02%42.00%) with ~85% of metabolites having CV<15% (FIG. 4).

Statistical Analysis

Figure 6A:
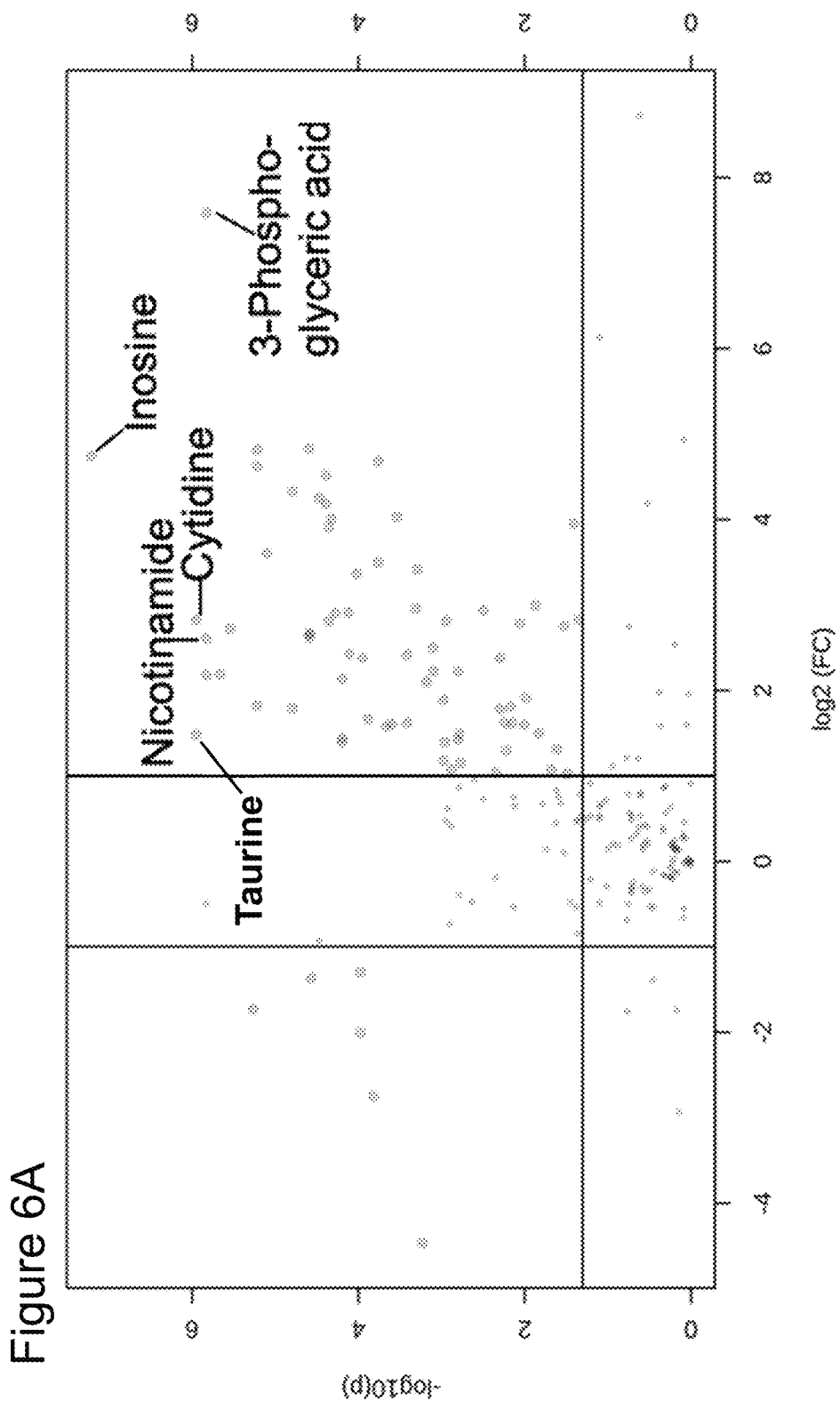
FIG. 6A and FIG. 6B, depicts volcano plots of plasma and urine metabolites. Five exemplary metabolites are labeled. Fold change (FC) threshold: 2.0; p-value threshold: 0.05. Unequal group variance was assumed, non-parametric test was used.
Figure 6B:
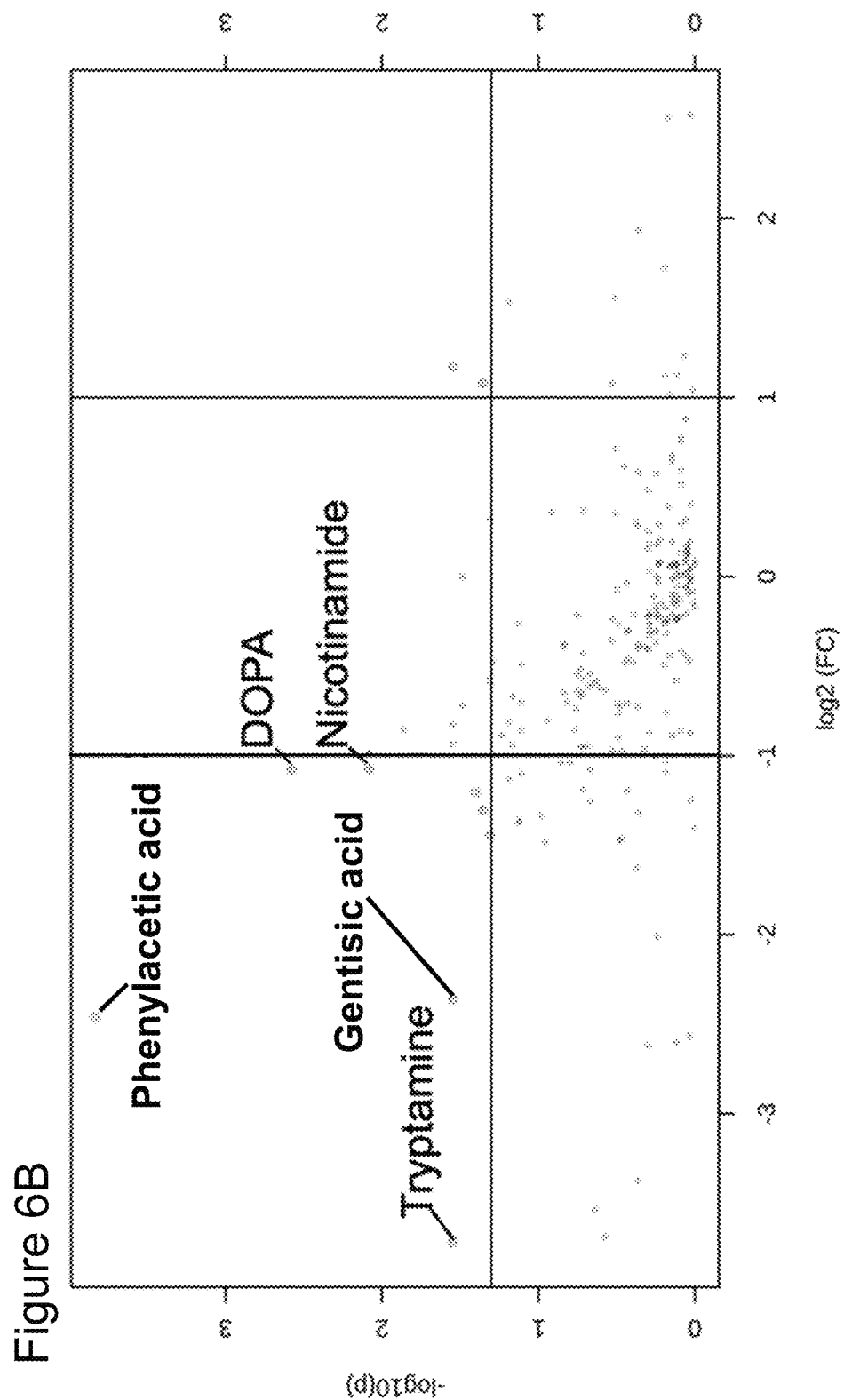
Figure 7A:
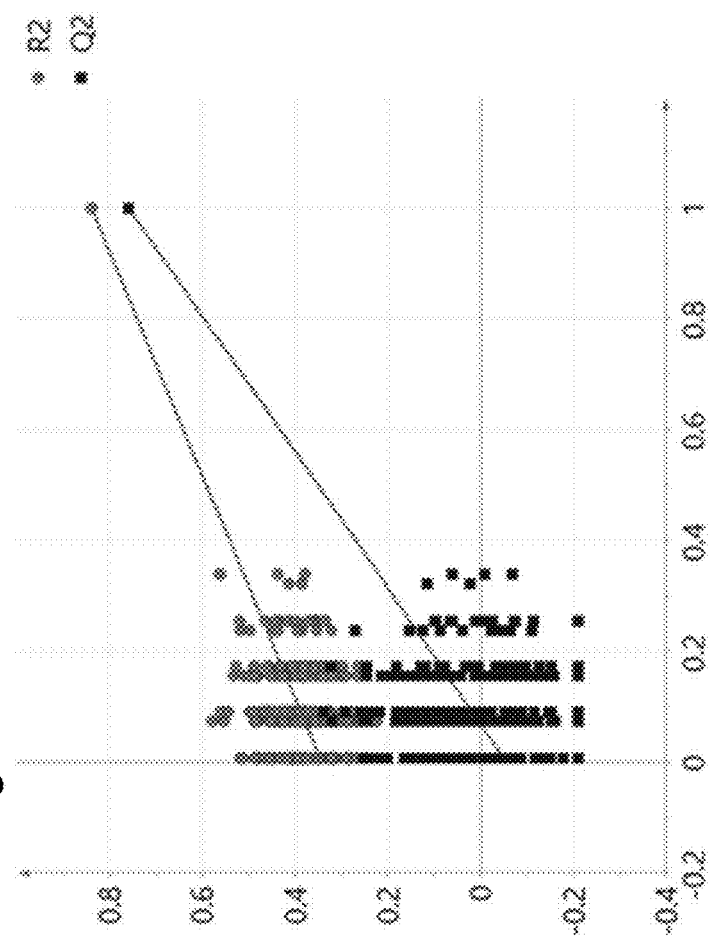
FIG. 7A through FIG. 7D, depicts results of partial least squares-discriminant analysis (PLS-DA) performed on $\log_{10}$-transformed plasma and urine metabolite data.
Figure 7B:
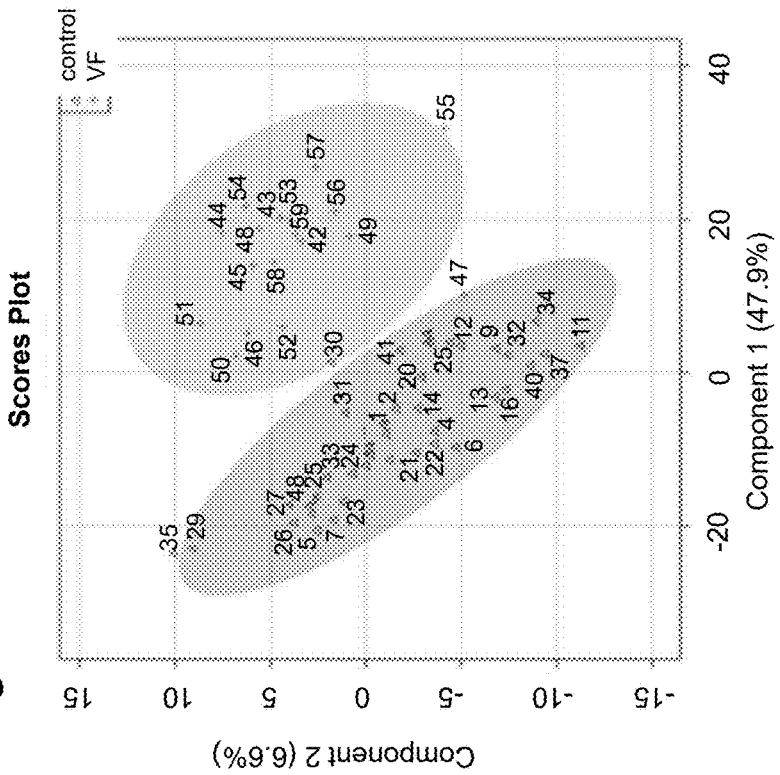
Figure 7C:
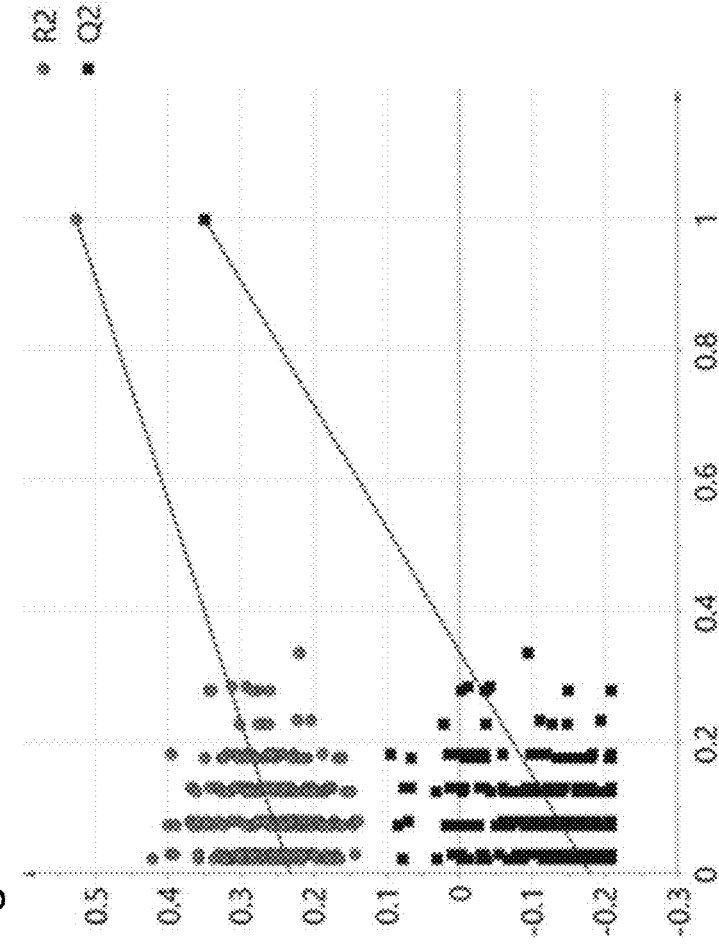
Figure 7D:
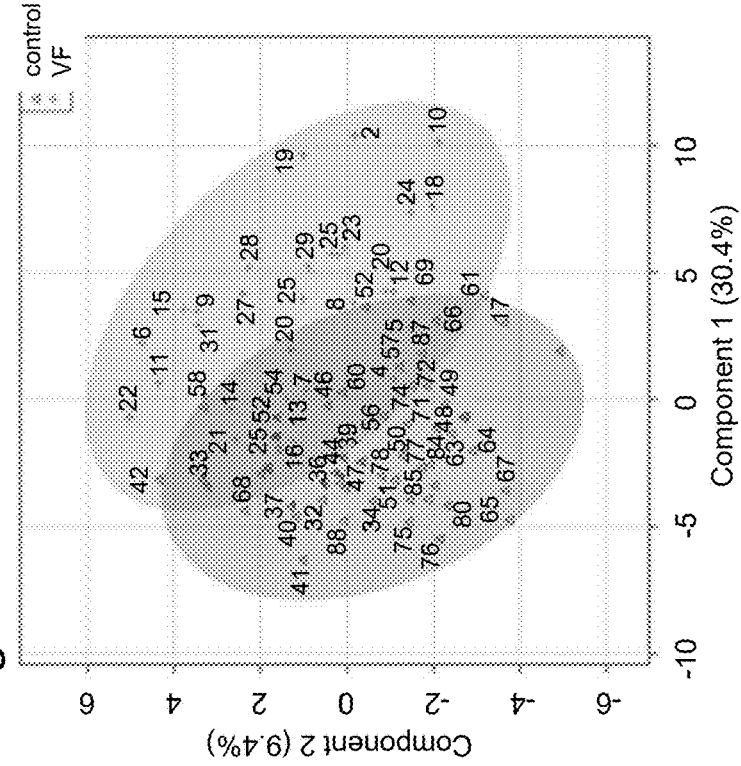

Of the 207 reliably detected plasma metabolites, 106 showed statistical significance between VF patients and non-VF counterparts, as determined by a Wilcoxon rank rum test (see Table 2 for the complete list of significant plasma metabolites, their associated p- and q-values, and directional changes). Of the 231 reliably detected urine metabolites (FIG. 5), 20 metabolites showed statistical significance between VF patients and non-VF controls (Table 3). Volcano plots of the tested plasma and urine metabolites showing significance and fold change values are presented in FIG. 6.

TABLE 2

Complete list of plasma metabolites found to be significant between VF patients and non-VF controls ([a] Values are FDR-corrected).

| Metabolite | Mean (SD) of non-VF | Mean (SD) of VF | p-value | q-value [a] | VF/non-VF |
|---|---|---|---|---|---|
| Phenylpyruvic acid | 767.098 (909.487) | 2652.667 (1399.143) | <0.0001 | 0 | Down |
| m-Hydroxyphenylacetic acid | 5413.902 (4204.522) | 35754.333 (72110.464) | <0.0001 | 0 | Down |
| Phenylglyoxylic acid | 201.610 (206.345) | 5677.500 (13815.467) | <0.0001 | 0 | Down |
| 4-Ethylbenzoic acid | 3414.463 (1562.858) | 1789.611 (772.786) | <0.0001 | 0 | Up |
| Aconitic acid | 134894.098 (125561.923) | 614132.833 (704041.673) | <0.0001 | 0 | Down |
| Glucuronic acid | 10691.463 (8835.651) | 67688.000 (89264.837) | <0.0001 | 0 | Down |
| 3-Phosphoglyceric acid | 47.000 (65.085) | 9044.889 (10224.959) | <0.0001 | 0 | Down |
| Trehalose | 501.366 (733.602) | 12350.278 (21092.154) | <0.0001 | 0 | Down |
| Lactose | 1525.366 (2124.076) | 43415.333 (77212.041) | <0.0001 | 0 | Down |
| Mucic acid | 1695.073 (1834.075) | 32251.667 (81455.680) | <0.0001 | 0 | Down |
| UDP | 444402.707 (80869.195) | 315901.556 (61426.519) | <0.0001 | 0 | Up |
| Urate | 20902.341 (15600.697) | 8111.889 (15749.978) | <0.0001 | 0 | Up |
| Nicotinamide | 80973.098 (65498.482) | 491977.167 (341431.680) | <0.0001 | 0 | Down |
| Adenosine | 126.951 (290.795) | 2306.111 (8547.169) | <0.0001 | 0 | Down |
| Inosine | 8418.439 (20891.451) | 224975.056 (542154.620) | <0.0001 | 0 | Down |
| Cytidine | 6217.195 (8535.782) | 43821.722 (40874.749) | <0.0001 | 0 | Down |
| Serotonin | 574.354 (1471.699) | 13168.889 (16156.079) | <0.0001 | 0 | Down |
| Kynurenine | 67817.341 (48058.141) | 239900.333 (154387.537) | <0.0001 | 0 | Down |
| Acetylglucosamine | 2347.659 (1571.320) | 14808.556 (29497.084) | <0.0001 | 0 | Down |
| HIAA | 22163.146 (16978.735) | 100382.944 (67347.661) | <0.0001 | 0 | Down |
| Taurine | 445508.293 (319693.230) | 1242645.556 (546361.931) | <0.0001 | 0 | Down |
| Neopterin | 114.610 (92.163) | 2309.111 (6325.796) | <0.0001 | 0 | Down |
| N-Acetylneuraminic acid | 7837.854 (6214.353) | 48149.667 (65529.408) | <0.0001 | 0 | Down |
| Serine | 636530.805 (465498.745) | 191022.222 (122889.050) | <0.0001 | 0 | Up |
| ATP | 256.110 (429.587) | 3117.583 (6387.790) | <0.0001 | 0 | Down |
| 4,3-Cresotic acid | 543.024 (586.677) | 5591.889 (11345.426) | <0.0001 | 0.0001 | Down |
| Glutaconic acid | 57052.000 (51630.259) | 297695.111 (505144.435) | <0.0001 | 0.0001 | Down |
| Fumarate | 3904.537 (5361.854) | 10277.167 (6802.435) | <0.0001 | 0.0001 | Down |
| R5P | 1106.610 (1110.623) | 4854.000 (4039.972) | <0.0001 | 0.0001 | Down |
| Phosphocreatine | 276465.268 (175998.461) | 112381.611 (53614.620) | <0.0001 | 0.0001 | Up |
| Hypoxanthine | 36082.902 (59246.688) | 253440.500 (375073.278) | <0.0001 | 0.0001 | Down |
| Creatinine | 6806479.073 (4136343.484) | 18434021.389 (20597092.113) | <0.0001 | 0.0001 | Down |
| Cytosine | 774.220 (625.257) | 5823.667 (9532.608) | <0.0001 | 0.0001 | Down |
| Amiloride | 2137.073 (1768.553) | 32232.778 (41054.770) | <0.0001 | 0.0001 | Down |
| Acetyl-L-glutamine | 4870.244 (6320.621) | 36424.889 (90812.647) | <0.0001 | 0.0001 | Down |
| Acetylcarnitine | 15264397.5 (13906895.225) | 48325691.000 (34471688.498) | <0.0001 | 0.0001 | Down |
| Aspartate | 144548.439 (191390.440) | 36062.722 (62627.864) | <0.0001 | 0.0001 | Up |
| UDP-GlNAc | 254.341 (456.734) | 4096.278 (5193.289) | <0.0001 | 0.0001 | Down |
| GDP | 576.976 (995.162) | 3100.167 (2829.869) | <0.0001 | 0.0001 | Down |
| Valeric acid | 208295.902 (245995.384) | 30966.944 (20154.547) | <0.0001 | 0.0002 | Up |
| Sorbitol | 7562.390 (5745.078) | 85457.889 (170824.541) | <0.0001 | 0.0002 | Down |
| alpha-KG/Adipic acid | 115687.195 (128604.182) | 352055.167 (285924.094) | <0.0001 | 0.0002 | Down |
| Decanoylcarnitine | 801675.390 (1206714.705) | 2395290.889 (2373922.031) | <0.0001 | 0.0002 | Down |
| Kynurenic acid | 1168.439 (1742.876) | 29907.111 (106962.679) | <0.0001 | 0.0002 | Down |
| cGMP | 17250.720 (57975.418) | 281385.417 (414126.069) | <0.0001 | 0.0003 | Down |
| 2-Methylglutaric acid | 48112.439 (52466.834) | 147715.167 (117705.465) | <0.0001 | 0.0004 | Down |
| Galactonic acid | 15268.390 (13596.163) | 81456.444 (176100.084) | <0.0001 | 0.0004 | Down |
| Xanthurenic acid | 577.561 (1182.061) | 4491.278 (10014.180) | 0.0001 | 0.0005 | Down |
| 1-Methyladenosine | 146860.110 (223884.636) | 1567914.056 (5396571.157) | 0.0001 | 0.0005 | Down |
| PGE2 | 7240.659 (7896.321) | 327.056 (311.300) | 0.0001 | 0.0006 | Up |
| Dimethylarginine | 508.085 (486.202) | 2174.889 (2436.668) | 0.0002 | 0.0006 | Down |
| 3-hydroxybutyric acid | 528.049 (614.555) | 2467.000 (4048.681) | 0.0002 | 0.0008 | Down |
| Adenine | 1776.171 (1480.568) | 10018.111 (20253.545) | 0.0002 | 0.0008 | Down |
| Glyoxylic acid | 1218.951 (1550.379) | 4513.944 (5186.019) | 0.0003 | 0.001 | Down |
| Pantothenic acid | 30854.073 (50997.288) | 81098.944 (135081.935) | 0.0003 | 0.0011 | Down |
| Xanthosine | 858.146 (674.404) | 6030.611 (12327.632) | 0.0003 | 0.0011 | Down |
| Glycylproline | 9499.390 (26184.445) | 13175.778 (13036.061) | 0.0003 | 0.0011 | Down |
| Glucosamine | 2389.927 (10952.810) | 5410.278 (9793.262) | 0.0003 | 0.0011 | Down |
| 4-Hydroxybenzaldehyde | 2147.829 (1240.685) | 3290.556 (1814.624) | 0.0003 | 0.0012 | Down |
| Lactate | 606008.780 (614066.590) | 1276734.722 (692832.013) | 0.0004 | 0.0013 | Down |
| dTMP | 12302.317 (9428.154) | 7404.556 (4089.898) | 0.0004 | 0.0013 | Up |
| Leucic acid | 4765.829 (6196.919) | 12796.389 (11703.913) | 0.0005 | 0.0016 | Down |
| Gluconic acid | 10084.341 (10236.700) | 47173.444 (107661.401) | 0.0005 | 0.0016 | Down |
| 3-Phenyllactic acid | 2753.146 (1797.324) | 6114.111 (4379.643) | 0.0006 | 0.0017 | Down |
| Pyruvate | 3138.463 (7788.109) | 5717.611 (6128.526) | 0.0005 | 0.0017 | Down |
| Cystine | 36519.659 (64288.908) | 102764.111 (90411.819) | 0.0005 | 0.0017 | Down |
| Anthranilic acid | 1743.927 (1377.783) | 1256.833 (2604.669) | 0.0008 | 0.0024 | Up |

TABLE 2-continued

Complete list of plasma metabolites found to be significant between VF patients and non-VF controls ([a] Values are FDR-corrected).

| Metabolite | Mean (SD) of non-VF | Mean (SD) of VF | p-value | q-value [a] | VF/non-VF |
|---|---|---|---|---|---|
| 6-Methyl-DL-Tryptophan | 6758.220 (7758.716) | 13139.889 (8471.394) | 0.0008 | 0.0025 | Down |
| Ethylmalonic acid | 562.878 (929.142) | 4316.889 (11022.810) | 0.0011 | 0.0032 | Down |
| Imidazole | 93276.585 (24883.531) | 70857.722 (17972.566) | 0.0011 | 0.0032 | Up |
| Methylhistamine | 11390.195 (6269.223) | 18930.167 (8901.474) | 0.0011 | 0.0032 | Down |
| 4-Pyridoxic acid | 288231.634 (983543.794) | 251933.556 (840323.263) | 0.0016 | 0.0045 | Up |
| Allopurinol | 1760.098 (1664.661) | 3616.778 (3950.359) | 0.0016 | 0.0045 | Down |
| Methyl α-D-glucopyranoside | 526.732 (575.170) | 2747.556 (4814.640) | 0.0019 | 0.0051 | Down |
| 3-Aminobutyric acid | 23391.122 (20558.345) | 80367.556 (122804.668) | 0.0019 | 0.0051 | Down |
| 5-Hydroxytryptophan | 1914.585 (1785.209) | 5871.944 (6218.323) | 0.0021 | 0.0057 | Down |
| Isovaleric acid | 48101.854 (46856.729) | 118393.056 (101307.610) | 0.0023 | 0.006 | Down |
| D-Galacturonic acid | 9832.439 (11294.956) | 34362.667 (49976.537) | 0.0026 | 0.0066 | Down |
| Normetanephrine | 4696.244 (3267.454) | 14385.833 (26929.888) | 0.0027 | 0.007 | Down |
| Nicotinate | 1080.488 (4749.259) | 1816.222 (2754.319) | 0.003 | 0.0075 | Down |
| 3-hydroxykynurenine | 18325.195 (10047.178) | 28709.500 (14933.541) | 0.0031 | 0.0076 | Down |
| Gibberellic acid | 446.854 (435.723) | 3078.611 (5795.638) | 0.0036 | 0.0088 | Down |
| 2-Aminoadipic acid | 13945.220 (13192.151) | 42123.056 (51884.925) | 0.0041 | 0.0099 | Down |
| Erythrose | 4974.683 (4671.148) | 18720.500 (38448.715) | 0.0043 | 0.0104 | Down |
| Mandelic acid | 2177.000 (1745.405) | 17376.556 (45442.269) | 0.0057 | 0.0135 | Down |
| Phenylbutazone | 8580.000 (15741.924) | 24277.222 (87556.855) | 0.0063 | 0.0148 | Down |
| 2-Pyrrolidinone | 5364.439 (3554.457) | 8560.778 (23304.948) | 0.007 | 0.0163 | Down |
| Phthalic acid | 3431.049 (5447.462) | 3774.222 (12035.429) | 0.0078 | 0.018 | Down |
| DOPA | 4966.098 (7481.359) | 10435.000 (21778.280) | 0.0091 | 0.0207 | Down |
| Maleic acid | 10884.463 (7215.685) | 14780.056 (6056.841) | 0.0106 | 0.0235 | Down |
| Pyroglutamic acid | 906652.000 (659064.874) | 1619928.611 (1308957.236) | 0.0106 | 0.0235 | Down |
| Xylose | 4946.024 (7334.651) | 12278.111 (13914.277) | 0.0111 | 0.0245 | Down |
| 2-Aminobutyric acid | 2172414.488 (1325623.343) | 3700377.389 (2526935.169) | 0.0117 | 0.0255 | Down |
| Ribose | 11512.146 (7202.911) | 18516.333 (8366.034) | 0.0126 | 0.0271 | Down |
| Suberic acid | 5126.341 (3361.662) | 34565.944 (74238.831) | 0.0142 | 0.03 | Down |
| Cadaverine | 29193.512 (17452.927) | 31284.000 (65752.635) | 0.0142 | 0.03 | Down |
| beta-Hydroxyisovaleric acid | 21565.610 (22788.207) | 43948.278 (40332.407) | 0.0156 | 0.0327 | Down |
| Glycine | 73422.415 (43287.510) | 52689.944 (36160.433) | 0.0172 | 0.0355 | Up |
| Azelaic acid | 4294.366 (4658.546) | 66508.111 (264243.763) | 0.019 | 0.0389 | Down |
| Homoserine/Threonine | 1535813.927 (825122.781) | 1054702.444 (530221.831) | 0.0207 | 0.0415 | Up |
| 5-Aminolevulinic acid | 989197.756 (843115.074) | 1372020.833 (659096.468) | 0.0207 | 0.0415 | Down |
| Malonic acid | 9420.439 (9521.260) | 66877.833 (122333.866) | 0.0226 | 0.0442 | Down |
| Hydroxyproline | 1052729.122 (939096.019) | 1457822.056 (736465.080) | 0.0226 | 0.0442 | Down |
| Glutamic acid | 1173856.000 (1266873.298) | 653706.000 (892982.804) | 0.0226 | 0.0442 | Up |
| Ketoleucine | 21780.976 (20912.018) | 37558.278 (35324.800) | 0.0237 | 0.0458 | Down |
| Oxaloacetic acid | 12333.049 (13049.461) | 17882.667 (8632.556) | 0.0247 | 0.0474 | Down |

TABLE 3

Urinary metabolites found to be statistically significant ($q < 0.05$) between VF patients and non-VF controls, using non-parametric t-test ([a] Unequal group variance assumed; [b] Data were normalized by creatinine levels; [c] Adjusted p-value cutoff: 0.05; [d] Non-parametric Wilcoxon rank-sum test used to adjust for multiple comparisons; [e] Calculated as mean ratio of metabolites: VF/control).

| Correction [a] | Metabolite [b] | p [c] | q [d] | Fold Change [e] |
|---|---|---|---|---|
| Mann-Whitney | Phenylacetic acid | 6.3E−7 | 1.4E−4 | 0.181 |
| | DOPA | 2.2E−5 | 0.0026 | 0.474 |
| | Nicotinamide | 1.0E−4 | 0.0082 | 0.475 |
| | Amino valerate | 1.6E−4 | 0.0082 | 0.380 |
| | Glycocyamine | 1.7E−4 | 0.0082 | 0.379 |
| | 6-Hydroxynicotinic acid | 3.5E−4 | 0.0138 | 0.347 |
| | Tryptamine | 0.0011 | 0.0284 | 0.076 |
| | Gentisic acid | 0.0011 | 0.0284 | 0.194 |
| | Glyoxylic acid | 0.0012 | 0.0284 | 2.257 |
| | Suberic acid | 0.0012 | 0.0284 | 0.367 |
| | 3-Methyl-2-oxovaleric acid | 0.0013 | 0.0284 | 0.339 |
| | 4-Ethylbenzoic acid | 0.0017 | 0.0325 | 0.315 |
| | p-Coumaric acid | 0.0018 | 0.0325 | 0.191 |
| | N,N-Dicyclohexylurea | 0.0023 | 0.0395 | 0.434 |
| | F16BP | 0.0030 | 0.0443 | 0.404 |
| | Dimethylarginine | 0.0030 | 0.0443 | 2.117 |
| | Tetracaine | 0.0038 | 0.0491 | 0.367 |
| | Urocanic acid | 0.0040 | 0.0491 | 0.290 |
| | Xanthosine | 0.0042 | 0.0491 | 0.282 |
| | Urate | 0.0042 | 0.0491 | 0.153 |

Figure 8B:
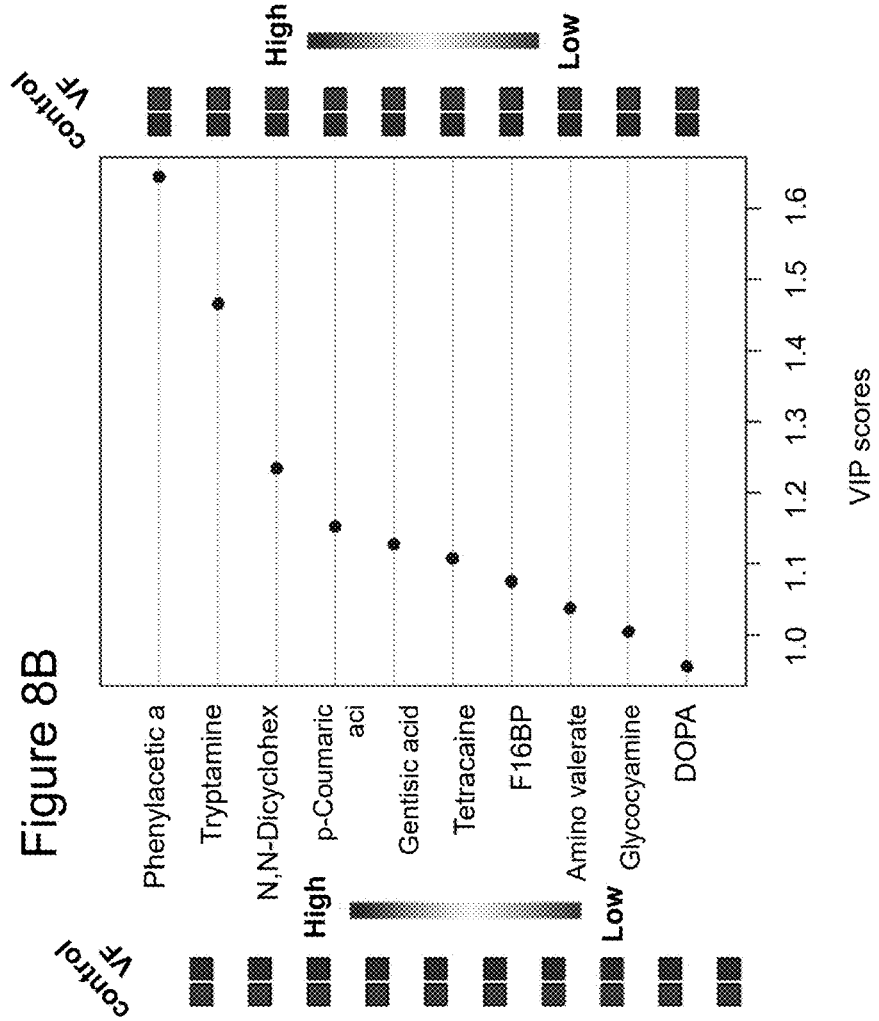
FIG. 8A and FIG. 8B, depicts Variable Importance in Projection (VIP) scores of plasma and urine partial least squares-discriminant analysis (PLS-DA) models constructed using 106 and 20 metabolites, respectively, for discrimination between Valley fever patients and non-Valley fever controls. Ten exemplary contributors to model projection are shown.
Figure 8A:
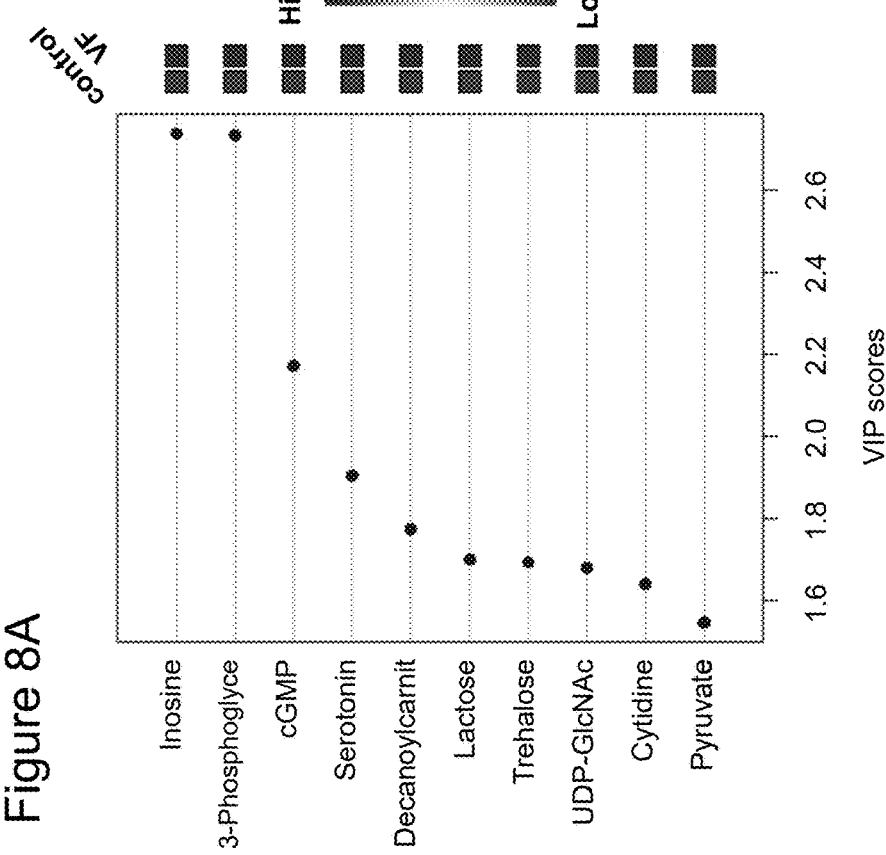
Figure 9A:
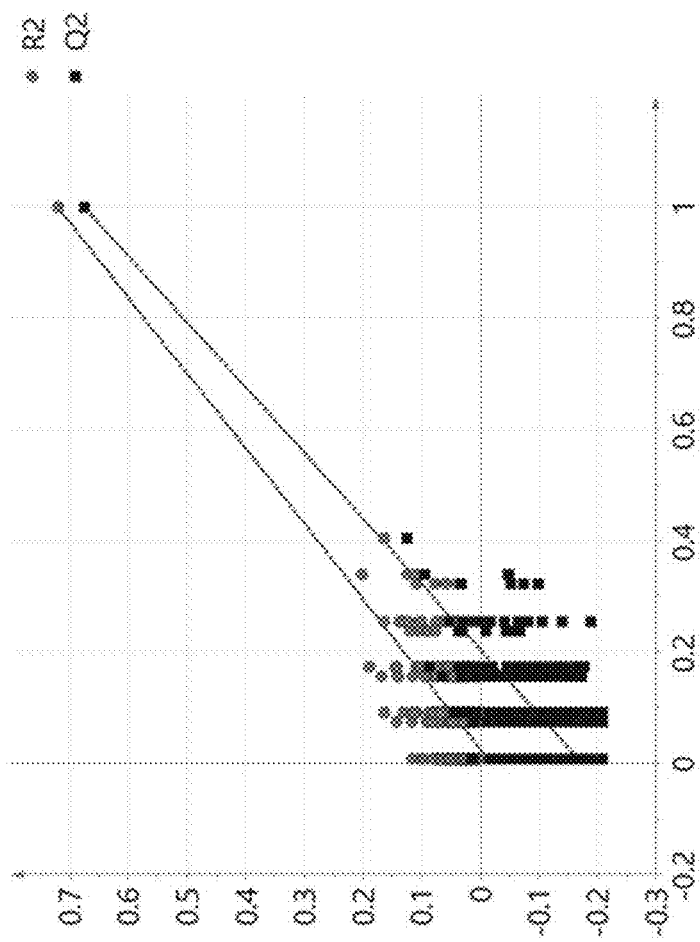
FIG. 9A through FIG. 9D, depicts results of orthogonal partial least squares-discriminant analysis (OPLS-DA) performed on $\log_{10}$-transformed plasma and urine metabolite data.
Figure 9B:
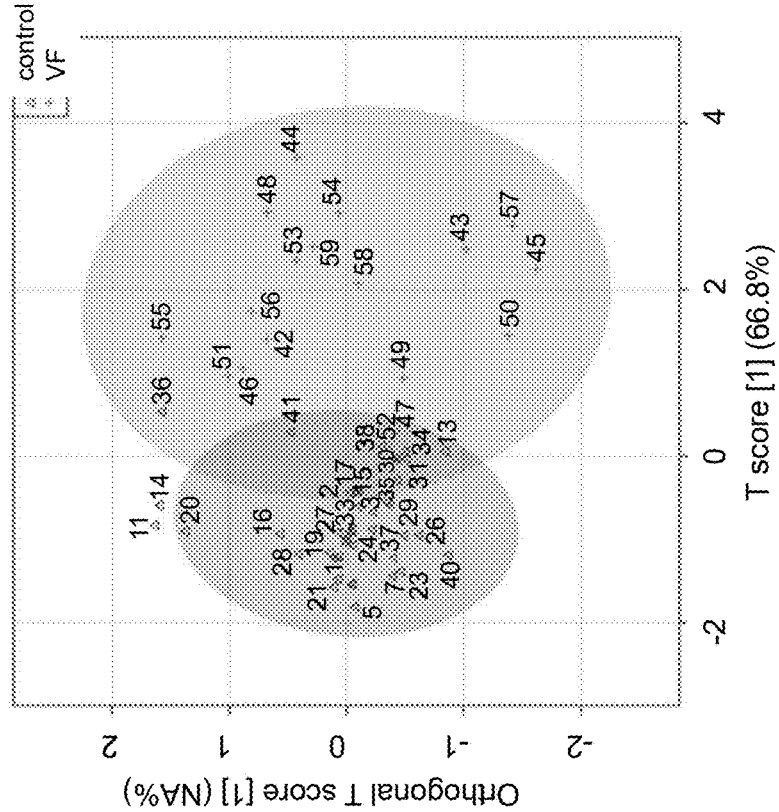
Figures 9C, 9D:
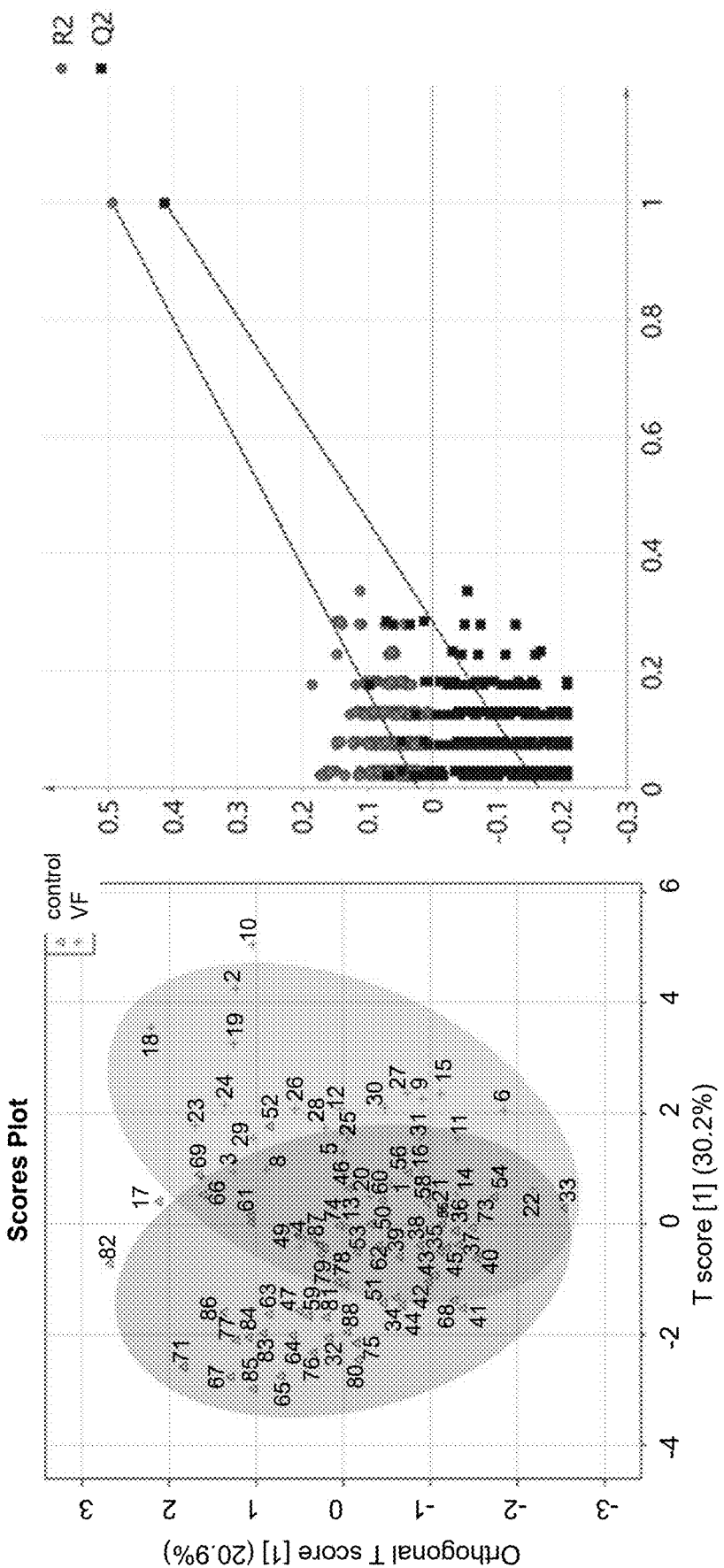

To further explore potential biomarkers for discrimination between VF patients and non-VF controls, levels of the 106 significant plasma metabolites and 20 significant urine metabolites were selected to establish initial partial least squares-discriminant analysis (PLS-DA) models. As can be seen in FIG. 7, a separation trend was observed in the initial PLS-DA score plots. The plasma PLS-DA model (FIG. 7A and FIG. 7B) showed superior predictive and explanatory capacity to the PLS-DA model constructed from significant urine metabolites (FIG. 7C and FIG. 7D) as validated by permutation testing with 200 iterations (Plasma: $R^2X$ (cum)=0.973, $R^2Y$ (cum)=0.862, $Q^2$ (cum)=0.789; Urine: $R^2X$ (cum)=0.847, $R^2Y$ (cum)=0.627, $Q^2$ (cum)=0.501). Variable importance in projection (VIP) scores were obtained from the initial PLS-DA models. As shown in FIG. 8 and FIG. 9, plasma metabolites were observed to have VIPs>2, and 9 urine metabolites had VIPs>1.

Figure 10:
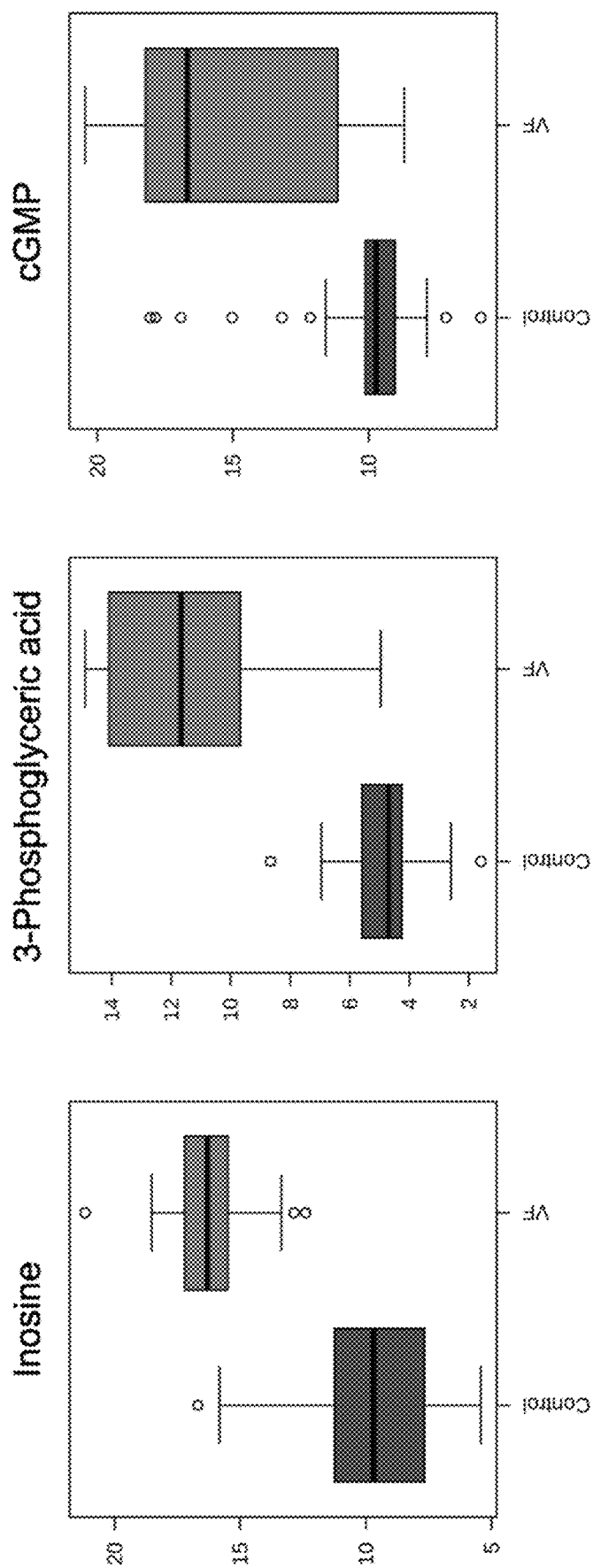
FIG. 10 depicts box plots of candidate plasma markers (all q<0.001 and VIP>2) for VF detection. Data were $\log_{10}$ normalized.
Figure 11:
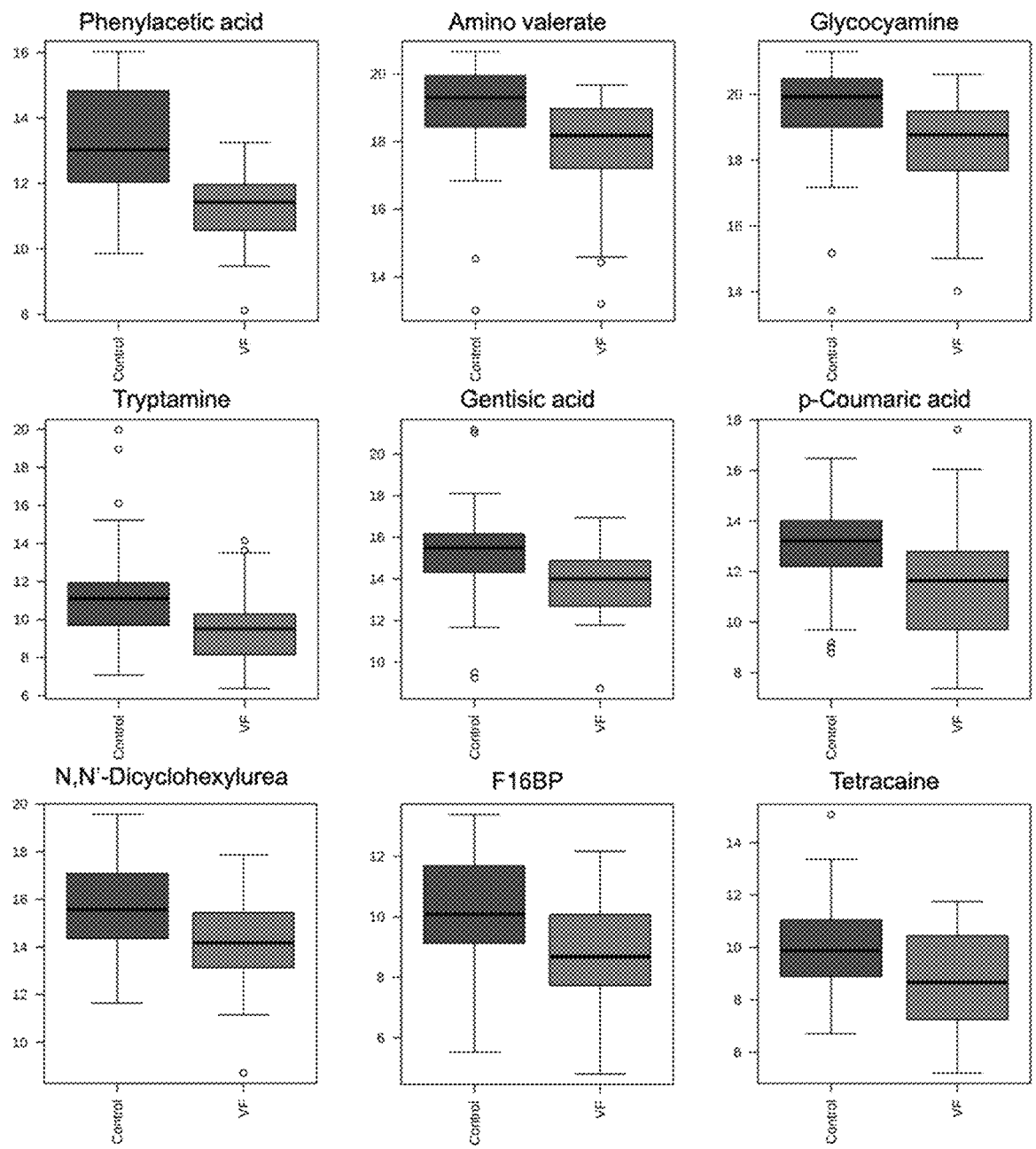
FIG. 11 depicts box plots of candidate urine markers (all q<0.05 and VIP>1) for VF detection. Data were $\log_{10}$ normalized.

In an effort to develop thrifty models that rely on the fewest number of predictors while accounting for as much variance as possible, enhanced orthogonal partial least squares-discriminant analysis (OPLS-DA) models were constructed using the 3 plasma metabolites that were both significant (q<0.001) and had VIPs>2 and the 9 urine metabolites that were significant (q<0.05) and had VIPs>1, respectively. As shown in FIG. 9, separation was clearly observed in both the plasma and urine OPLS-DA models, with the plasma metabolite model again outperforming the urinary model (Plasma: $R^2X$ (cum)=0.668, $R^2Y$ (cum)= 0.739, $Q^2$ (cum)=0.723; Urine: $R^2X$ (cum)=0.302, $R^2Y$ (cum)=0.416, $Q^2$ (cum)=0.389]. Significance information and fold change values for the final panel of 3 plasma and 9 urine metabolites can be found in Table 4; box plots of the plasma biomarker panel are provided in FIG. 10, while urine biomarkers are plotted in FIG. 11.

TABLE 4

Significance and fold change details for final panel of plasma and urine markers.

| Metabolite | Plasma | | Urine | |
| --- | --- | --- | --- | --- |
| | FDR q | Fold Change | FDR q | Fold Change |
| Inosine | <0.0001 | 26.724 | | |
| 3-Phosphoglyceric acid | <0.0001 | 192.44 | | |
| cGMP | 0.0003 | 16.312 | | |
| Phenylacetic acid | | | 1.4E−4 | 0.181 |
| Amino valerate | | | 0.0082 | 0.380 |
| Glycocyamine | | | 0.0082 | 0.379 |
| Tryptamine | | | 0.0284 | 0.076 |
| Gentisic acid | | | 0.0284 | 0.194 |
| p-Coumaric acid | | | 0.0325 | 0.191 |
| N,N'-Dicyclohexylurea | | | 0.0395 | 0.434 |
| F16BP | | | 0.0443 | 0.404 |
| Tetracaine | | | 0.0491 | 0.367 |

Figure 12B:
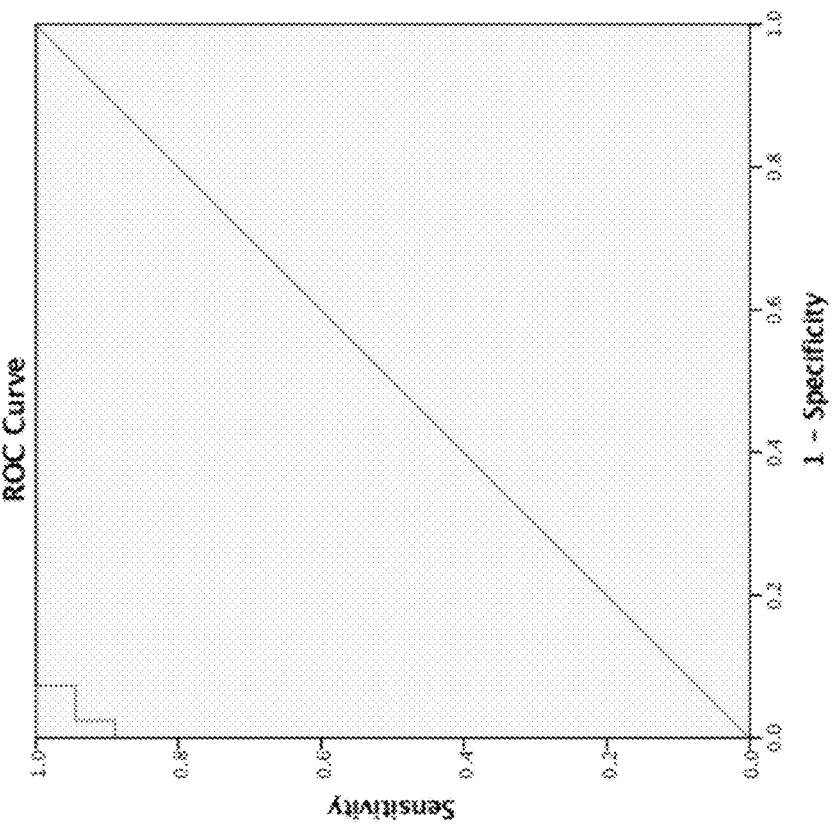
FIG. 12A and FIG. 12B, depicts results of evaluation of model classification performance using ROC analysis.
Figure 12A:
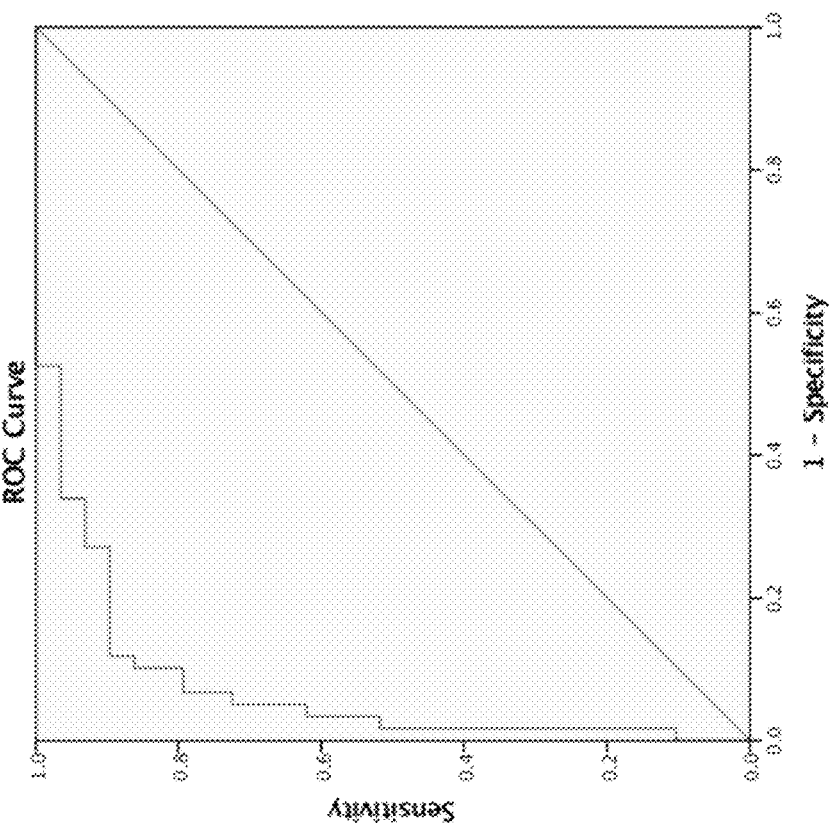

Receiver operating characteristic (ROC) analysis was performed to determine the classification performance of the enhanced plasma and urine OPLS-DA models. As evidenced by the ROC curve shown in FIG. 12A, the OPLS-DA model constructed using only 3 significant and important plasma metabolites demonstrated near-perfect classification accuracy (AUC=0.995), excellent sensitivity (0.994) and specificity (0.976). The OPLS-DA model constructed using the 9 significant and important urine metabolites also showed excellent overall accuracy (AUC=0.929), high sensitivity (0.897) and good specificity (0.881) (FIG. 12B).

To analyze the discriminatory ability of the plasma and urine biomarker panels in accurately detecting VF patients of varying clinical course and seropositivity, univariate significance testing was performed on the plasma metabolite panel (inosine, 3-phosphoglyceric acid, cGMP) and urinary metabolite panel (phenylacetic acid, tryptamine, N,N-dicyclohexylurea, p-coumaric acid, gentisic acid, tetracaine, fructose-1,6-bisphosphate, amino valerate, glycocyamine) to monitor any potential changes in their levels attributable to clinical course or serology status. Notably, the results presented herein showed no significant change in these 12 marker candidates between VF patients with acute, chronic, or disseminated disease or VF patients with positive, negative, or indeterminant serology results (all p>0.10).

Pathway Analysis of Metabolic Data

Figure 13A:
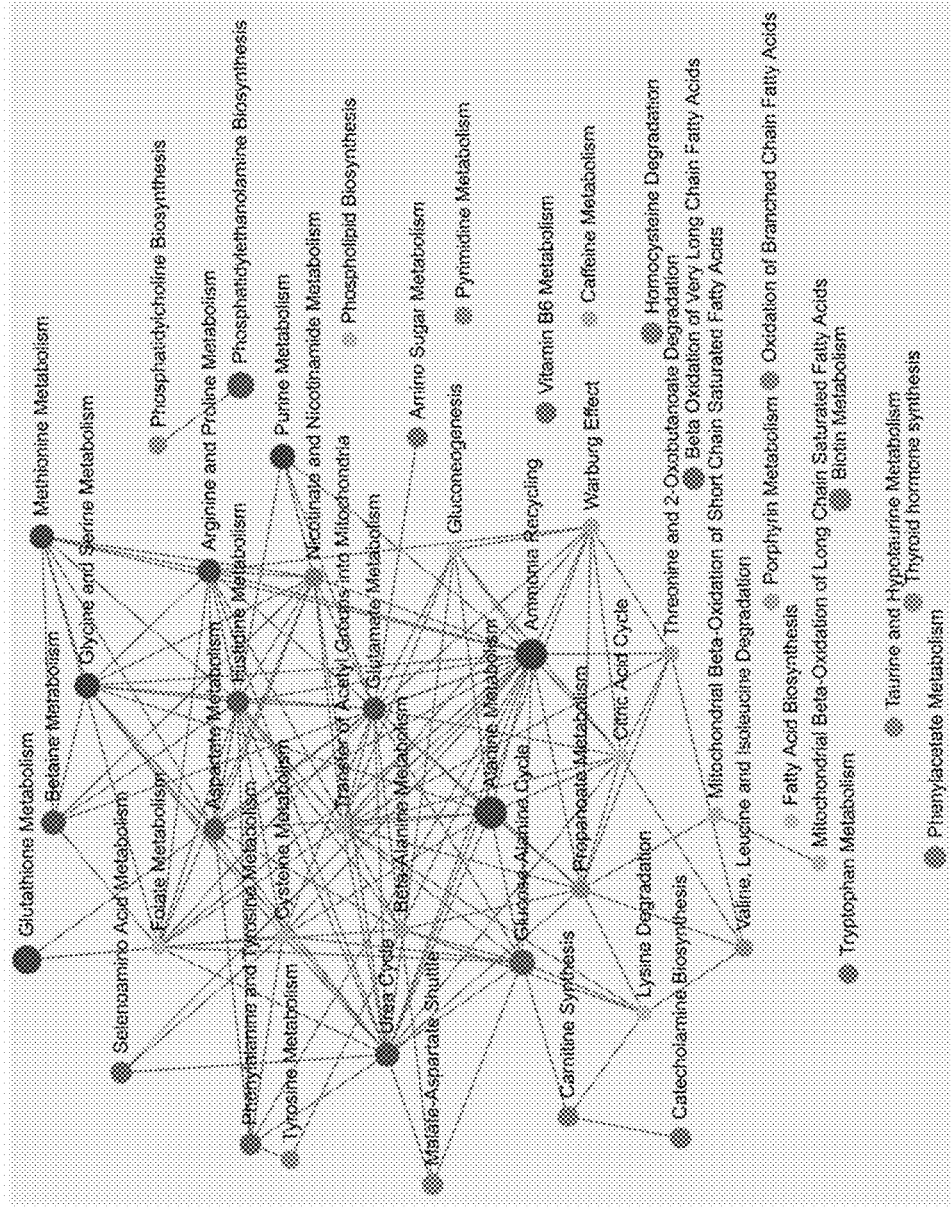
FIG. 13A and FIG. 13B, depicts results of enrichment analysis of metabolic data.
Figure 13B:
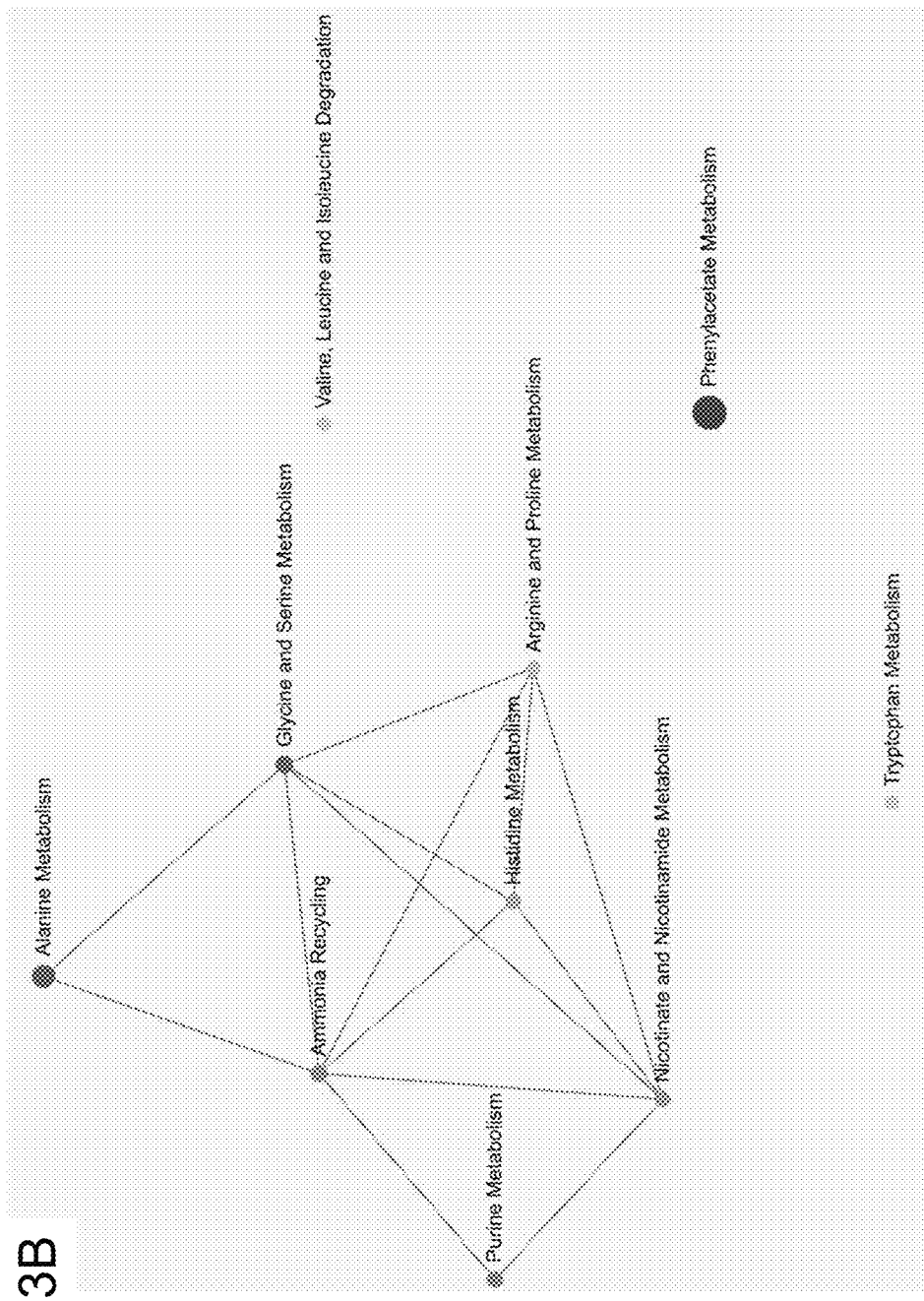

Enrichment analysis was conducted using KEGG database searches and metabolite intensities for both plasma and urine data. Enrichment analysis of 207 reliably detected plasma metabolites showed significant (p) disturbances in alanine metabolism (0.005) and amino sugar metabolism (0.014). Enrichment analysis of 231 reliably detected urine metabolites was also conducted. Although non-significant, results indicated a high magnitude of fold enrichment (VF/control) in phenylacetate metabolism (0.167) and alanine metabolism (0.315). Enriched pathways as determined by analysis of all reliably detected plasma and urine metabolites are shown as separated motifs in FIG. 13.

Figure 14A:
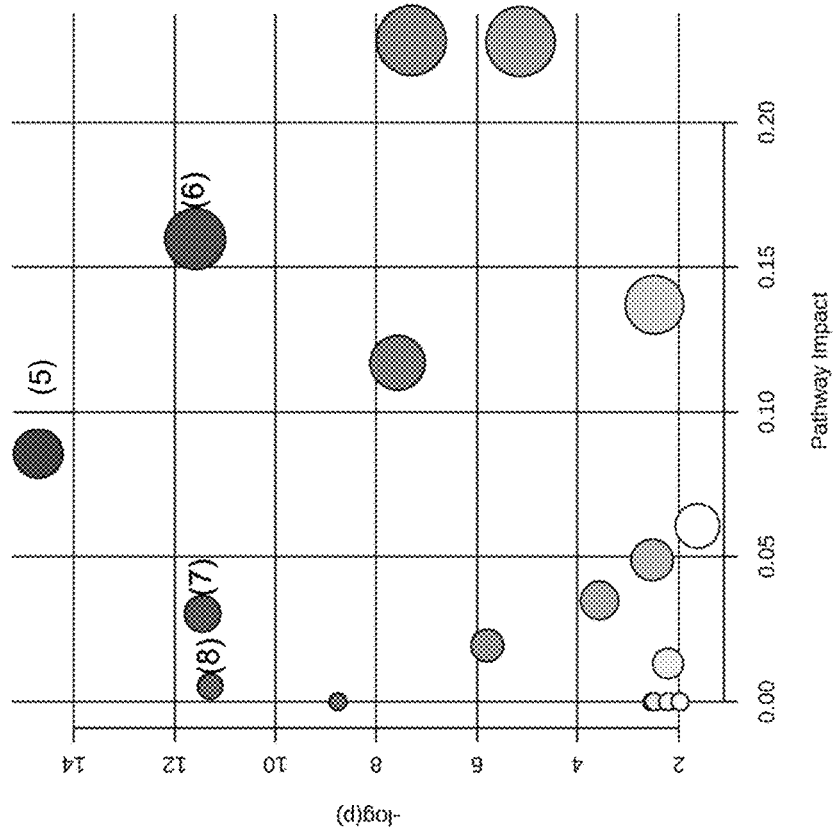
FIG. 14A and FIG. 14B, depicts the metabolome view of pathway analysis of metabolic data comparing VF patients and controls. Data were $\log_{10}$-transformed prior to analysis.
Figure 14B:
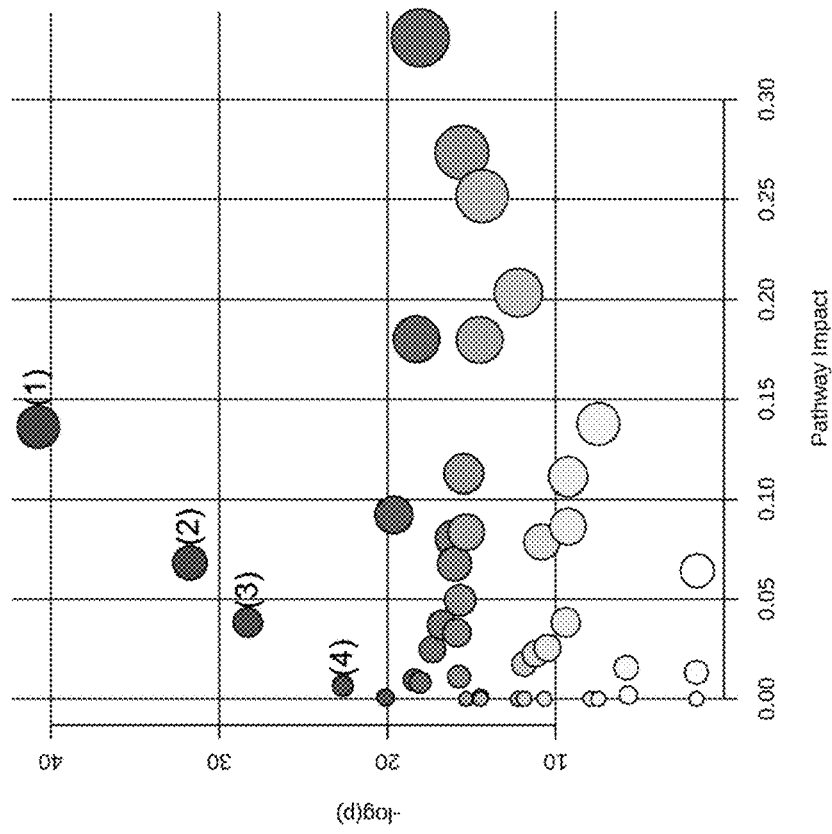

Pathway analysis was also performed in order to determine significantly affected pathways in VF patients. Although no pathway was observed to have large impact coefficients (>0.50), 4 pathways were shown to be significantly affected in both plasma and urine samples (FIG. 14). Agreement between plasma and urinary analyses revealed significant disturbances in nicotinate and nicotinamide metabolism and ammonia recycling.

Roughly 10% of patients who contract VF will develop serious chronic diseases or potentially fatal disseminated diseases. Diagnosis of VF remains difficult as currently available diagnostic techniques are inaccurate, nonspecific, and time-consuming. As a result, various diagnostic techniques must be used in conjunction for detection of VF, increasing cost and time to diagnosis. Significant metabolic alterations have previously been shown in response to various fungal infections and have demonstrated potential for use as diagnostic biomarkers. For the last two decades, significant innovations in mass spectrometry-based metabolic profiling and analysis of disease-related alterations have been made and, in doing so, these efforts have borne highly sensitive and valuable diagnostic information. In the current study, a combination of targeted metabolic profiling and multivariate statistical analysis was explored for the discovery of sensitive and specific metabolite biomarkers for relatively rapid VF detection. This particular method was used to detect 207 plasma metabolites and 231 urine metabolites from many relevant metabolic pathways. This multi-step biomarker selection, model construction, and cross validation have demonstrated the robust diagnostic power of this metabolic profiling method in this study of 147 subjects.

Although a number of studies have performed mass spectrometry-based proteomic and transcriptomic analysis for detection of biological alterations in response to coccidioidomycosis infection, no study has, to date, applied metabolomics for the accurate detection of coccidioidomycosis in humans. The targeted LC-MS/MS metabolite profiling approach, presented in Example 1, determined 3 significantly altered plasma metabolites with FDR q<0.001 and VIP>2 and 9 urine metabolites with FDR q<0.05 and VIP>1, which informed the construction of enhanced OPLS-DA models for the diagnosis of VF. The combination of these 3 plasma metabolites had a diagnostic sensitivity and specificity of 94.4% and 97.6%, respectively, with an AUC of 0.995. Additionally, the urine panel of 9 metabolites provided a diagnostic sensitivity of 89.7% and specificity of 88.1%, with an AUC of 0.929. Although this urine panel was less accurate than the plasma panel, it represents an increase in diagnostic accuracy over currently available urinary antigen tests, which only report sensitivity of around 70%. While efforts also focus on combining the plasma and urine biomarkers into a single statistical model, the realization of such a model was not possible in the current example given that paired plasma and urine samples were only collected from one patient, and on different days. Therefore, example 1 focused on the development of thrifty, independent models given the available data. Moreover, the current time-to-diagnosis ranges from a few days using skin-testing methods, which are contingent on an immune response and cannot differentiate current and past infections, to an unacceptably long period of 2 weeks in the case of laboratory culture. In contrast, herein described metabolomics approach has great potential to achieve accurate diagnosis of VF within 24 hours. Therefore, these results suggest that metabolomics methods can provide a notable improvement to VF diagnosis over currently available serological diagnostics.

Importantly, no significant differences in levels of the 12 marker candidates were observed between VF patients with acute, chronic, or disseminated disease or VF patients with positive, negative, or indeterminant serology results, indicating that both the plasma and urine metabolite panels achieved accurate diagnoses of VF irrespective of clinical course or serological status. Acutely ill patients were detected, indicating that these metabolic markers are present early in infection. Likewise, patients who were chronically ill or had disseminated diseases were also detected, suggesting that these markers persist and are present in extrapulmonary diseases.

Although candidate markers presented in this study are capable of accurate VF diagnosis irrespective of stage, and therefore fulfill a critical need in current diagnostic testing, subsequent studies focus on the development of an ideal biomarker panel capable of identifying disease course that further aids clinical decisions. In order to reach this level of analysis, metabolic biomarker panels should be designed with special attention paid to characterizing differential, stage-dependent metabolites.

In addition, herein described metabolite-based diagnosis approach was correct in identification of seronegative patients. These patients were clinically determined to have VF by the Mayo Clinic Arizona diagnostic rubric but were negative by at least one serological test. Frequently, these seronegative or serologically indeterminant patients are symptomatic and have positive radiography and/or histology tests, further complicating the process of differential diagnosis. These cases represent a difficult to diagnose subset of patients and, therefore, an assay that can correctly assess these patients is of critical need. Results of the herein described urinary and plasma biomarker panels demonstrate the significant potential of this LC/MS-MS method to accurately classify this subset of patients.

Although previously unreported in association with Valley fever, several of the plasma and urinary biomarkers identified in this diagnostic assay have been shown to be critical in the initiation and propagation of related fungal diseases. Chitty and colleagues showed production of inosine via adenylosuccinate lyase to be essential for DNA and RNA synthesis as well as energy production of *Cryptococcus neoformans* in a murine model. In another murine model, Alves de Castro et. al. demonstrated cGMP to be a vital component of Sch9, a serine/threonine kinase responsible for target of rapamycin (TOR) signaling, essential for virulence of *Aspergillus fumigatus*. In the current study, levels of inosine were found to be increased more than 26-fold in VF patients, whereas levels of cGMP exhibited a 16-fold increase between VF patients and controls. Furthermore, phenylacetic acid has been shown to severely limit the proliferative capacity of *Rhizoctonia solani* in plants. Similarly, p-coumaric acid was recently demonstrated to significantly inhibit the growth of *Colletotrichum* spp. in vitro. Levels of both metabolites were decreased by nearly 90% in VF patients as compared to controls. Additionally, fructose-1,6-bisphosphate (F16BP) has been shown to prevent mortality from active *Candida albicans* bloodstream infection in mice. Interestingly, levels of F16BP were reduced by almost 60% in VF patients as compared to controls. Further investigation of these candidate markers and their role in *Coccidioides* virulence and survival in a host environment is warranted.

While results of plasma and urine enrichment analyses are commensurate with each other, they have not been previously reported in the literature in regard to VF. Enrichment analysis of plasma and urine data indicated significant and high-impact changes, respectively, in alanine metabolism. Additionally, analysis of plasma data indicated significant enrichment in amino sugar metabolism, while analysis of urine metabolites revealed a more than two-fold reduction in phenylacetate metabolism in response to active VF infection. Therefore, the significant differences and high magnitude effects observed herein provide valuable target pathways for future experimental studies.

The current understanding of the primary and secondary metabolites produced by *Coccidioides* sp. is limited, but metabolism is known to be a key factor in pathogenesis. Sharpton et. al. used genomic sequencing evidence to suggest that coccidioidal genetic diversion away from its closest genetic relative, *Uncinocarpus reesii* (a non-pathogen), is at least partially the result of acquiring and adapting genes involved in metabolism, membrane biology, and mycotoxin production. They hypothesized that these changes led to metabolic and morphological phenotypes that enabled survival within a living host, ultimately resulting in disease. Interestingly, they found that the subtilisin N domain-containing gene family of serine proteases were significantly increased in fungi of the order Onygenales. Serine proteases have not only been implicated in the pathogenicity of *Aspergillus fumigatus*, but also more recently a serine/threonine protein kinase and a serine/threonine phosphatase suggested to be involved in *C. posadasii* virulence. An avirulent cps1 knockout strain of *C. posadasii* had 7-fold less serine/threonine protein kinase and 3-fold less serine/threonine phosphatase transcription by RNA-seq than its virulent wild-type parent. It is therefore not surprising that glycine and serine metabolism was found to be significantly disturbed in plasma and urine from VF patients in this study.

Both plasma and urinary analyses in this study revealed significant increases in nicotinamide metabolism and ammonia recycling. Increased nicotinamide may be a general host response to fungal infection, as it is involved in innate immune cell function and has previously been shown to decrease enzyme activity in *Candida* and *Trichophyton* spp. infections. Nicotinamide is currently being investigated for an antifungal therapeutic strategy, as it was shown to cause a loss of cell viability and reduce virulence in a mouse model of *C. albicans* infection. On the other hand, increased ammonia recycling could be a coccidioidal mechanism to evade host immune defenses and maximize nitrogen utilization to support the high demand of amino acid synthesis of rapidly dividing cells during infection, similar to that in cancer cells. *Coccidioides* spp. grow in alkaline soil conditions, and they convert the pH of the pulmonary microenvironment to alkaline concentrations during infection by releasing ammonia and urease when spherules rupture during the parasitic cycle. Ammonia and urease elicit a nonprotective innate host inflammatory response which contributes significantly to pathogenesis by inducing host cell damage without clearing the fungus. Mice infected with a *C. posadasii* strain with double mutant knockout with deleted urease and ureidoglycolate hydrolase, an enzyme upstream of ammonia synthesis from allantoate, were significantly less virulent and showed increased survival and better granuloma formation than the wild-type controls.

These proof-of-concept diagnostic metabolites are encouraging; however, there are a number of limitations that need to be addressed in future studies. Firstly, none of the non-VF plasma samples and only 2 of the non-VF urine samples tested (1 bacterial pneumonia of an unknown species and 1 fungal pneumonia due to *Candida* sp. with *Microascus* sp.) had non-VF CAP. Although there were no false positive reactions in these 2 non-VF CAP patients, a greater number of this type of patients should be evaluated, as any diagnostic for VF should discern VF from other pneumonial etiologies including bacterial, viral, and other fungal pneumonia-causing genera like *Histoplasma, Blastomyces, Aspergillus*, and Cryptococcal spp. Secondly, a relatively homogenous population of patients residing in Arizona was assessed. The most prevalent *Coccidioides* sp. in Arizona is *C. posadasii*, whereas in California *C. immitis* is more prevalent. Additional VF positive samples should be collected from California and South America and evaluated for possible metabolite variation between strains and patients of different regions. Additionally, further studies need to be performed to discriminate whether these significantly produced metabolites are generated by the host or pathogen. Although this determination is not essential for diagnostic purposes, metabolite biomarkers produced by the host are more likely to be variable in heterogeneic patient groups with varying comorbidities, whereas metabolites produced by the pathogen should be more consistently present. If particular metabolites could be attributed to the pathogen, novel inhibitors of metabolic precursors could be investigated as therapeutic targets. Future studies that evaluate metabolite production and consumption from in vitro *Coccidioides* spp. fungal cultures or mouse infection studies can help determine pathogen specific metabolites and metabolic pathways for targeted treatment.

This study is part of a growing body of literature in which an MS-based method has been utilized for disease biomarker discovery and accurate diagnosis. Furthermore, this is the first metabolomics approach for coccidioidomycosis diagnosis. Additionally, in lieu of applying database searches for compound annotation in global profiling, all targeted metabolites reported in this study were tested with pure standard compounds, allowing for improved relative quantification and analytical precision. Results of these fold change analysis, significance testing, as well as enrichment and pathway analyses indicate metabolites and pathways previously shown to be crucial for immune response inhibition, reproduction, dissemination and pathogenic severity of fungal diseases, broadly defined. Likewise, the metabolites and associated metabolic pathways identified in this study may inform the development of new antifungal treatments for Valley fever.

In this study, comparisons of plasma and urine metabolites from VF patients and non-VF controls were performed using a targeted LC-MS/MS metabolic profiling approach and significant alterations in a variety of the metabolites were detected. These results demonstrate the utility of a panel of 3 plasma metabolites with FDR q-values $<0.001$ and VIPs>2 and 9 urine metabolites with q-values $<0.05$ and VIPs>1 for the rapid and accurate diagnosis of VF. These differential metabolites were used to construct predictive classification models that showed high sensitivity, specificity, and overall performance for VF patients of all clinical courses, including seronegative patients. Application of bioinformatic methods expanded basic knowledge of the metabolome related to VF and showed ubiquitous disturbances in glycine and serine metabolism that could be targeted therapeutically in future studies. As evidenced by the results presented in Example 1, this metabolic profiling method can potentially serve as a novel approach for rapid and routine VF diagnosis, with significant advantages to current diagnostic methods. In addition, this study provides a strong basis for larger multi-site projects to validate findings across different population groups and further advances the development of improved clinical care for VF patients.

In summary, coccidioidomycosis, also known as Valley fever (VF), is a potentially lethal fungal infection that results in more than 200 deaths per year in the United States. Despite the important role of metabolic processes in the molecular pathogenesis of VF, robust metabolic markers to enable effective screening, rapid diagnosis, accurate surveillance, and therapeutic monitoring of VF are still lacking. Example 1 presents a targeted liquid chromatography-tandem mass spectrometry (LC-MS/MS)-based metabolic profiling approach for identifying metabolic marker candidates that could enable rapid, highly sensitive and specific VF detection. Using this targeted approach, 207 plasma metabolites and 231 urinary metabolites from many metabolic pathways of potential biological significance were reliably detected and monitored in 147 samples taken from two groups of subjects (48 VF patients and 99 non-VF controls). The results of the univariate significance testing and multivariate model development informed the construction of a 3-metabolite panel of potential plasma biomarkers and a 9-metabolite panel of potential urinary biomarkers. Receiver operating characteristic (ROC) curves generated based on orthogonal partial least squares-discriminant analysis (OPLS-DA) models showed excellent classification performance, with 94.4% sensitivity and 97.6% specificity for plasma metabolites. Urine metabolites were less accurate, demonstrating 89.7% sensitivity and 88.1% specificity. Enrichment, pathway, and network analyses revealed significant disturbances in glycine and serine metabolism, in both plasma and urine samples. This is the first study aiming to discover novel metabolite markers of VF, which could achieve accurate diagnosis within 24 hrs. The results expand basic knowledge of the metabolome related to VF and potentially reveal pathways or markers that could be targeted therapeutically. This study also provides a promising basis for the development of larger multi-site projects to validate the findings across population groups and further advance the development of better clinical care for VF patients.

The materials and methods employed in these experiments are now described.

Experimental Section

Reagents

Acetonitrile (ACN), methanol (MeOH), ammonium acetate ($NH_4OAc$), and acetic acid (AcOH), all LC-MS grade, were purchased from Fisher Scientific (Pittsburgh, PA). Ammonium hydroxide ($NH_4OH$) was bought from Sigma-Aldrich (Saint Louis, MO). DI water was provided in-house by a Water Purification System from EMD Millipore (Billerica, MA). Phosphate buffered saline (PBS) was bought from GE Healthcare Life Sciences (Logan, UT). Standard compounds corresponding to the measured metabolites were purchased from Sigma-Aldrich (Saint Louis, MO) and Fisher Scientific (Pittsburgh, PA).

Sample Collection and VF Diagnostic Criteria

The samples were collected under a previously approved IRB protocol with waived consent. Urine and plasma specimens were acquired from excess clinical specimens collected for routine standard of care at Mayo Clinic Arizona. De-identified aliquots were provided to the Arizona Metabolomics Laboratory (College of Health Solutions, Arizona State University) for processing. Samples had been frozen under −80° C. until analysis. VF status was determined based on clinical evaluation using the Mayo Clinic Arizona multi-factorial criteria for the diagnosis of Coccidioidomycosis. This diagnostic rubric includes the evaluation of patient symptoms, radiography, serology, histology and culture results, as no single assay or measure can currently be used alone to diagnose VF.

Sample Preparation

Frozen plasma and urine samples were first thawed overnight under 4° C. Afterward, 50 μL of each plasma sample was placed in a 2 mL Eppendorf vial while 100 μL of each urine sample was placed in a separate vial. For both plasma and urine, the initial step for protein precipitation and metabolite extraction was performed by adding 500 μL MeOH and 50 μL internal standard solution (containing 1,810.5 μM 13C3-lactate and 142 μM 13C5-glutamic acid). The mixture was then vortexed for 10 s and stored at −20° C. for 30 min, followed by centrifugation at 14,000 RPM for 10 min at 4° C. The supernatants (450 μL and 500 μL for plasma and urine, respectively) were collected into new Eppendorf vials and dried using a CentriVap™ (vacuum concentrator system) Concentrator (Labconco, Fort Scott, KS). Alternatively, the samples were dried at 38° C. The dried samples were reconstituted in 150 μL of 40% PBS/60% ACN and centrifuged again at 14,000 RPM at 4° C. for 10 min. After that, 100 μL of supernatant was collected from each sample into an LC autosampler vial for subsequent analysis. Two pooled samples, which were a mixture of all plasma and urine samples respectively, were used as the internal quality-control (QC) samples and injected once every 10 experimental samples.

LC-MS/MS

The targeted LC-MS/MS method used here was modeled after that developed and used in a growing number of studies. Briefly, all LC-MS/MS experiments were performed on an Agilent™ 1290 UPLC-6490 QQQ-MS system (Santa Clara, CA). Each sample was injected twice, 10 μL for analysis using negative ionization mode and 4 μL for analysis using positive ionization mode. Both chromatographic separations were performed in hydrophilic interaction chromatography (HILIC) mode on a Waters XBridge™ BEH Amide column (150×2.1 mm, 2.5 μm particle size, Waters Corporation, Milford, MA). The flow rate was 0.3 mL/min, auto-sampler temperature was kept at 4° C., and the column compartment was set to 40° C. The mobile phase was composed of Solvents A (10 mM ammonium acetate, 10 mM ammonium hydroxide in 95% $H_2O$/5% ACN) and B (10 mM ammonium acetate, 10 mM ammonium hydroxide in 95% ACN/5% $H_2O$). After an initial 1 min isocratic elution of 90% B, the percentage of Solvent B decreased to 40% at t=11 min. The composition of Solvent B was maintained at 40% for 4 min (t=15 min), after which the percentage of B gradually went back to 90%, to prepare for the next injection.

The mass spectrometer was equipped with an electrospray ionization (ESI) source. Targeted data acquisition was performed in multiple-reaction-monitoring (MRM) mode. 118 and 160 MRM transitions were monitored in negative and positive mode, respectively (278 transitions in total). The whole LC-MS system was controlled by Agilent™ MassHunter™ Workstation software (Santa Clara, CA). The extracted MRM peaks were integrated using Agilent™ MassHunter™ Quantitative Data Analysis software (Santa Clara, CA).

Data Analysis

Univariate testing was performed using SPSS 22.0 (SPSS Inc., Chicago, IL). Multivariate statistical analyses were performed using open-source R software and SIMCA-P (Umetrics, Umeå, Sweden). The data were $\log_{10}$-transformed prior to model construction. Pathway analysis and integrating enrichment analysis were performed and visualized using the online MetaboAnalyst software.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of determining if a human subject has an indication of having coccidioidomycosis (Valley fever), the method comprising:
   a) obtaining a plasma sample from a human subject;
   b) measuring the level of 3-phosphoglyceric acid (3-PG) in the plasma sample of the human subject;
   c) determining a mean level of 3-PG in plasma samples acquired from a population of healthy human subjects known not to have coccidioidomycosis;
   d) comparing the measured level of 3-PG in the plasma sample to the mean level of 3-PG in plasma samples acquired from a population of healthy human subjects known not to have coccidioidomycosis; and
   e) determining that there is an indication that the human subject has coccidioidomycosis if the measured level of 3-PG in the plasma sample is greater than the mean level of 3-PG in plasma samples acquired from a population of healthy human subjects known not to have coccidioidomycosis.

2. The method of claim 1, wherein the method comprises using a multi-dimensional non-linear algorithm to determine if the measured level of 3-PG in the plasma sample of the human subject is statistically greater than the mean level of 3-PG in plasma samples acquired from a population of healthy human subjects known not to have coccidioidomycosis.

* * * * *